US007569208B2

(12) United States Patent
Kohno et al.

(10) Patent No.: US 7,569,208 B2
(45) Date of Patent: Aug. 4, 2009

(54) DIAGNOSTIC AGENTS FOR PANCREATIC EXOCRINE FUNCTION

(75) Inventors: Tadashi Kohno, Kanagawa (JP); Isaburo Hosoi, Saitama (JP); Junko Hirayama, Kanagawa (JP); Kunihiko Shibata, Chiba (JP); Asuka Ito, Kanagawa (JP)

(73) Assignee: Tokyo Gas Company Limited, Tokyo (JP)

( * ) Notice: Subject to any disclaimer, the term of this patent is extended or adjusted under 35 U.S.C. 154(b) by 0 days.

(21) Appl. No.: 11/643,608

(22) Filed: Dec. 20, 2006

(65) Prior Publication Data
US 2007/0189966 A1   Aug. 16, 2007

Related U.S. Application Data

(62) Division of application No. 10/926,544, filed on Aug. 25, 2004, now abandoned, which is a division of application No. 09/589,419, filed on Jun. 7, 2000, now Pat. No. 6,905,668, which is a division of application No. 09/401,739, filed on Sep. 23, 1999, now Pat. No. 6,254,851.

(51) Int. Cl.
*A61K 51/00* (2006.01)
*A61M 36/14* (2006.01)

(52) U.S. Cl. .................. 424/1.81; 424/1.11; 424/1.65; 424/1.73

(58) Field of Classification Search ................ 424/1.11, 424/1.37, 1.65, 1.73, 1.81, 9.1, 9.3, 9.4, 9.5, 424/9.6, 9.7, 9.8; 536/1.11
See application file for complete search history.

(56) References Cited

U.S. PATENT DOCUMENTS

| | | | |
|---|---|---|---|
| 3,786,140 A | 1/1974 | Meyer-Bertenrath et al. | |
| 3,917,812 A | 11/1975 | Woog et al. | |
| 4,676,974 A | 6/1987 | Hofmann et al. | |
| 5,300,280 A | 4/1994 | DeRosch et al. | |
| 5,393,660 A | 2/1995 | Kitahata et al. | |
| 5,405,975 A | 4/1995 | Kuhn et al. | |
| 5,640,014 A | 6/1997 | Sauke et al. | |
| 6,254,851 B1 * | 7/2001 | Kohno et al. | 424/1.81 |
| 6,905,668 B1 * | 6/2005 | Kohno et al. | 424/1.81 |
| 7,125,683 B2 * | 10/2006 | Asuka et al. | 435/18 |

FOREIGN PATENT DOCUMENTS

| | | |
|---|---|---|
| DE | 4426204 A1 | 1/1995 |
| DE | 1981 2332AI | 9/1999 |
| EP | 0220951 | 5/1987 |
| GB | 2 251 381 A | 7/1992 |
| JP | 6-315399 | 11/1994 |

OTHER PUBLICATIONS

EP Search Report for EP991307554 dated Jan. 26, 2000.
New Zealand Examination report for NZ No. 337946 dated Sep. 28, 1999.
Decisions on Esau's Application 49 RPC 85, Montecantini Edison's Application [1972] RPC 639 and Electrical Musical Industries Application 56 RPC 39, 41.
Acheson et al., The American Journal of Clinical Nutrition, 41: 881-890 (1985).
Dewit et al., Pediatric research, 32 (1) 45-49 (1992).
Goromaru et al., Biol Pharm. Bull., 17(1): 156-159 (1994).
Harding et al., Isotonpenpraxis Environ. Health Stud., 30: 108 (1994).
Heile et al., Biomedical and environmental Mass Spectrometry, 16: 133-135 (1998).
Hiele et al, J. Lab Clin. Med., 112(2): 193-200 (1988).
Hiele et al., Gastroenterology, 96:503-509(1989).
Hiele et al., Gut., 31:175-178 (1990).
Kohmoto et al., Biosci, Biotech, Biochem, 56(6): 937-940 (1992).
Jindrich et al.:Carbohydrate Research 266 (1995) 75-80.
Lewis, Sr., Hawley's Condensed Chemical Dictionary, 12th Edition, p. 217, 1993.
Löser et al., Z. Gastroenterol, 35:187-194 (1977).
Normand et al., American Journal of Clinical Nutrition, 55: 430-435 (1992).
Rating. et al, European Journal of Pediatrics, XX, Springer Verlag, vol. 156, pp. 18-23, (1997).
Shulman et al, Pediatric Research, 20(8) 740-743 (1986).
Tao et al., Biochimica et Biophysica Act, 995: 214-220 (1989).
Weaver et al., British Journal of Nutrition, 74: 531-537 (1995).
Yu et al., Biochimica et Biophysica Acta, 1244:1-9 (1995).
Office Action for Japanese Patent Application No. H11-263300, mailed Mar. 19, 2007.

* cited by examiner

*Primary Examiner*—D. L Jones
(74) *Attorney, Agent, or Firm*—Finnegan, Henderson, Farabow, Garrett & Dunner, LLP

(57) ABSTRACT

The present invention provides a $^{13}C$-labeled oligosaccharide or polysaccharide or a salt thereof excluding U—$^{13}C$-maltose, $^{13}C$-starch, 1-$^{13}C$-maltotetraose and 1-$^{13}C$-amylose; a derivative of the $^{13}C$-labeled oligosaccharide or polysaccharide or salt thereof; a $^{13}C$-labeled inclusion complex or a salt thereof, which comprises a cyclodextrin or a modified derivative thereof as a host molecule; a $^{13}C$- or $^{14}C$-labeled fluorescein ester compound or a salt thereof; and a diagnostic agents for pancreatic exocrine function comprising these compounds $^{13}C$- or $^{14}C$-labeled.

18 Claims, 11 Drawing Sheets

Powder X-ray diffraction spectra of BPL / γ-C D (1:4) system (a) BPL ; (b) physical mixture ; (c) solid dispersion system.
The diffraction spectra of γ-C D is the same as Fig.

Powder X-ray diffraction spectra of BPLM / γ-C D (1:4) system (a) BPLM ; (b) γ-C D ; (c) physical mixture ; (d) solid dispersion system.

\* p < 0.05 (ANOVA with Fischer LSD)

\*\* p < 0.01 (ANOVA with Fischer LSD)

\* $p < 0.05$ (ANOVA with Fischer LSD)

\*\* $p < 0.01$ (ANOVA with Fischer LSD)

\*\*\* $p < 0.001$ (ANOVA with Fischer LSD)

DIAGNOSTIC AGENTS FOR PANCREATIC EXOCRINE FUNCTION

This is a division of application Ser. No. 10/926,544, filed Aug. 25, 2004 now abandoned, which is a divisional of application Ser. No. 09/589,419 filed Jun. 7, 2000, which is a divisional of application Ser. No. 09/401,739 filed Sep. 23, 1999, which in turn claims the benefit of Japanese Application Serial No. 271252 filed Sep. 25, 1998, Japanese Application Serial No. 271253 filed Sep. 25, 1998, Japanese Application Serial No. 261979 filed Sep. 16, 1999, and Japanese Application Serial No. 263300 filed Sep. 17, 1999 all of which are incorporated herein by reference. Application Ser. No. 09/410,739 matured into U.S. Pat. No. 6,254,851 on Jul. 3, 2001. Application Ser. No. 09/589,419 matured into U.S. Pat. No. 6,905,668 on Jun. 14, 2005.

BACKGROUND OF THE INVENTION

1. Field of the Invention

The present invention relates to novel compounds useful as diagnostic agents for pancreatic exocrine function and their use.

2. Background of the Invention

"Pancreatic exocrine function tests" are useful for the diagnosis of pancreatic diseases such as chronic and acute pancreatitis and pancreatic cancer. They are also useful to assess the condition and prognosis of patients and to control the medication: The general descriptions are found in Arvanitakis and Cooke, Gastroenterology, 74:932 (1978); Niederau and Grendell, Gastroenterology, 88:1973 (1985); Goldberg, Bull Mol. Biol. Med., 15:1 (1990); Lankisch, Int. J. Pancreatology. 14:9 (1993); Bank and Chow, Gastroenterologist, 2:224 (1994); and Steer et al., New Eng. J. Med., 332:1482 (1995).

At present, "Gold standard" of the pancreatic exocrine function test involves inserting a tube through the mouth to the duodenum to collect the duodenal juice. Now, the secretin test is generally utilized wherein secretin is intravenously administered to stimulate the secretion of the pancreatic juice prior to the collection. This method is highly accurate since the amount and components of the pancreatic juice are directly analyzed. However, this method can not be used repeatedly or used for screening because of the very strong stress caused on the subjects. It is available at only a relatively small number of medical centers having highly skilled physicians. Further, since this method requires fluoroscopic tube placement during the collection of the duodenal juice, there is the problem of X ray exposure.

On the other hand, a test for quantifying pancreatic exocrine enzymes from the pancreas into the blood is clinically employed for screening pancreatic diseases (The Merck Manual 16th edition). However, the increase of the pancreatic exocrine enzymes in the blood is only observed at the initial stage of acute pancreatitis or at the recrudescent stage of chronic pancreatitis and does not always reflect the ability of the pancreas to secrete pancreatic exocrine enzymes. Further, the increase of pancreatic exocrine enzymes in the blood may sometimes not be detected due to serum turbidity in pancreatitis accompanied by hyperlipemia.

Accordingly, simple methods which require no insertion of a tube are utilized for repetition and screening tests. One of them is the pancreolauryl test (PLT) wherein a synthetic substrate FDL (fluorescein diraulate, dilaurylfluorescein) for cholesterol ester hydrolase, esterase, secreted from the pancreas is orally administered and urine is accumulated for 10 hours followed by measuring the amount of a degradation product fluorescein excreted into the urine: U.S. Pat. No. 3,917,812; Barry et al., Lancet (1982) Oct. 2. p. 742; Scharpe and Iliano, Clin. Chem., 33:5 (1987). However, this method requires a long time to carry out the test and therefore can not often be performed on outpatients and is not suitable in physical examinations.

Under these circumstances, there is a need for the development of a simple method for testing the pancreatic exocrine function which imparts low stress on subjects and gives accurate results soon.

On the one hand, the $^{13}$C-breath test wherein a $^{13}$C-labeled starch is administered has been recently considered to be employed in the test for the pancreatic exocrine function: Hiele et al., Gastroenterology, 96:503 (1989); Dewit et al., Pediatric Res., 32:45 (1992); and Z. Gastroenterol., 35:187 (1997). In the enteric tract, starch is degraded efficiently to glucose by the cleavage at any internal α-1,4 glucoside linkage with α-amylase secreted from the pancreas and by the action of enzymes such as α-glucosidase (maltase) of mucosal epithelial cells of the small intestine and absorbed: Essentials of Human Metabolism, 2nd ed., W. C. McMurray, Harper & Row Publishers, NY. The $^{13}$C-breath test wherein a $^{13}$C-labeled starch is administered utilizes the phenomenon that after the $^{13}$C-labeled starch is degraded in the digestive tract, it is absorbed and decarboxylated by metabolic action in the body to generate $^{13}$CO$_2$ which is excreted into the breath, and it is a safe and simple method. However, any $^{13}$C-labeled oligosaccharide or polysaccharide other than $^{13}$C-labeled starch has not yet been studied.

Since there is an α-glucosidase (maltase) in mucosal epithelial cells of the small intestine, which cleaves a non-reducing terminal α-1,4-glucoside linkage (Enzyme Handbook, Springer-Verlag, Berlin), starch is degraded into glucose sequentially from the non-reducing terminal and absorbed only by the action of enzymes such as the α-glucosidase (maltase), even without the action of α-amylase. Thus, starch is subject to the action of a non-pancreatic-exocrine enzyme α-glucosidase (maltase) of mucosal epithelial cells of the small intestine and therefore the $^{13}$C-labeled starch breath test does not reflect the pancreatic exocrine function only. Accordingly, it would be more preferred if a substrate compound specific for α-amylase in the digestive tract is selected.

Accordingly, an object of the present invention is to provide a diagnostic agent for pancreatic exocrine function which leads to a test for the pancreatic exocrine function imparting low stress on subjects and yields the results in a short period of time.

It is another object, of the present invention to provide a diagnostic agent for pancreatic exocrine function which is specific to the α-amylase secretion ability.

It is a further object of the present invention to provide a novel compound, usable in the pancreatic exocrine function test.

SUMMARY OF THE INVENTION

The present inventors have found that the pancreatic exocrine function test can be carried out by orally administering a $^{13}$C-labeled oligosaccharide or a $^{13}$C-labeled inclusion complex or a $^{13}$C-labeled fluorescein ester compound to a rat with chronic pancreatitis and measuring the $^{13}$C-concentration in the exhaled CO$_2$ after administration. Thus, the present invention has been completed.

Accordingly, the present invention provides a labeled $^{13}$C-labeled oligosaccharide or polysaccharide or a salt thereof or a derivative thereof or a $^{13}$C-labeled inclusion complex other than U-$^{13}$C-maltose, $^{13}$C-starch, 1-$^{13}$C-maltotetraose and 1-$^{13}$C-amylose.

Also, the present invention provides a diagnostic agent for pancreatic exocrine function comprising a $^{13}$C- or $^{14}$C-labeled oligosaccharide or polysaccharide or a salt or a derivative thereof, or a $^{13}$C- or $^{14}$C-labeled inclusion complex or a salt thereof other than $^{13}$C-starch.

Moreover, the present invention provides a diagnostic agent for pancreatic exocrine function comprising a compound which is degraded with α-amylase but not degraded with α-glucosidase.

Furthermore, the present invention provides a $^{13}$C- or $^{14}$C-labeled fluorescein ester compound or a salt thereof.

Also, the present invention provides a diagnostic agent for pancreatic exocrine function comprising a $^{13}$C- or $^{14}$C-labeled fluorescein ester compound or a pharmaceutically acceptable salt thereof.

The subject matters of the present invention are as follows.

(1) A $^{13}$C-labeled oligosaccharide or polysaccharide or a salt thereof excluding U-$^{13}$C-maltose, $^{13}$C-starch, 1-$^{13}$C-maltotetraose and 1-$^{13}$C-anylose.

(2) The $^{13}$C-labeled oligosaccharide or polysaccharide or salt thereof according to (1), which is hydrolyzed with α-amylase.

(3) The $^{13}$C-labeled oligosaccharide or polysaccharide or salt thereof according to (2), which is not hydrolyzed with α-glucosidase.

(4) The $^{13}$C-labeled oligosaccharide or polysaccharide or salt thereof according to any one of (1) to (3), wherein at least one sugar molecule constituting the oligosaccharide or polysaccharide is $^{13}$C-labeled.

(5) The $^{13}$C-labeled oligosaccharide or polysaccharide or salt thereof according to any one of (1) to (3), wherein at least one sugar molecule constituting the oligosaccharide or polysaccharide is modified with at least one $^{13}$C-labeled modifying group.

6) The $^{13}$C-labeled oligosaccharide or polysaccharide or salt thereof according to any one of (1) to (5), which is a linear or branched oligosaccharide or polysaccharide.

(7) The $^{13}$C-labeled oligosaccharide or polysaccharide or salt thereof according to any one of (1) to (5), which is a cyclic oligosaccharide or polysaccharide.

(8) The $^{13}$C-labeled oligosaccharide or polysaccharide or salt thereof according to (6), which is modified at the non-reducing terminal.

(9) The $^{13}$C-labeled oligosaccharide or polysaccharide or salt thereof according to (1), which is a $^{13}$C-cyclodextrin or β-galactosyl-$^{13}$C-maltooligosaccharide.

(10) A derivative of the $^{13}$C-labeled oligosaccharide or polysaccharide or salt thereof according to any one of (1) to (9).

(11) A $^{13}$C-labeled inclusion complex or a salt thereof, which comprises a cyclodextrin or a modified derivative thereof as a host molecule.

(12) The inclusion complex or salt thereof according to (11), wherein the host molecule is $^{13}$C-labeled.

(13) The inclusion complex or salt thereof according to (11), wherein the guest molecule is $^{13}$C-labeled.

(14) The inclusion complex or salt thereof according to any one of (11) to (13), wherein the guest molecule is selected from the group, consisting of oligosaccharides, amino acids, peptides, organic acids, fatty acids, fatty acid glycerides, vitamins, catechins, carotinoids, flavonoids and cholesterol.

(15) The inclusion complex or salt thereof according to (14), wherein the guest molecule is selected from the group consisting of $^{13}$C-phenylalanine, benzoylphenylalanyl-$^{13}$C-leucine and benzoylphenylalanyl-$^{13}$C-leucine methyl ester.

(16) A diagnostic agent for pancreatic exocrine function comprising a $^{13}$C- or $^{14}$C-labeled oligosaccharide or polysaccharide or a salt thereof or a derivative thereof other than 13C-starch.

(17) The diagnostic agent for pancreatic exocrine function according to (16), wherein the $^{13}$C- or $^{14}$C-labeled oligosaccharide or polysaccharide or salt thereof or derivative thereof is hydrolyzed with α-amylase.

(18) The diagnostic agent for pancreatic exocrine function according to (17) wherein the $^{13}$C- or $^{14}$C-labeled oligosaccharide or polysaccharide or salt thereof or derivative thereof is not hydrolyzed with α-glucosidase.

(19) The diagnostic agent for pancreatic exocrine function according to any one of (16) to (18), wherein the $^{13}$C- or $^{14}$C-labeled oligosaccharide or polysaccharide is a linear or branched oligosaccharide or polysaccharide.

(20) The diagnostic agent for pancreatic exocrine function according to (19), wherein the $^{13}$C- or $^{14}$C-labeled oligosaccharide or polysaccharide is modified at the non-reducing terminal.

(21) The diagnostic agent for pancreatic exocrine function according to any one of (16) to (18), wherein the $^{13}$C- or $^{14}$C-labeled oligosaccharide or polysaccharide is a cyclic oligosaccharide or polysaccharide.

(22) A diagnostic agent for pancreatic exocrine function comprising a, $^{13}$C- or $^{14}$C-labeled inclusion complex or a salt thereof having a cyclodextrin or a modified derivative thereof as a host molecule.

(23) The diagnostic agent for pancreatic exocrine function according to any one of (16) to (22), wherein the pancreatic exocrine function to be diagnosed is the ability of the pancreas to secrete α-ainylase.

(24) The diagnostic agent for pancreatic exocrine function according to any one of (16) to (22), wherein the pancreatic exocrine function to be diagnosed is the ability of the pancreas to secrete α-amylase and at least one pancreatic exocrine enzyme other than α-amylase.

(25) A $^{13}$C- or $^{14}$C-labeled fluorescein ester compound or a salt thereof.

(26) The compound or salt thereof according to (25), which is a compound or salt thereof resulting from a reaction of a $^{13}$C- or $^{14}$C-labeled acid with fluorescein, at both or either of the two hydroxyl groups at 3' and 6' positions to form an ester linkage.

(27) The compound or salt thereof according to (26), wherein the acid is a carboxylic acid.

(28) The compound or salt thereof according to (27), wherein the carboxylic acid is a fatty acid.

(29) The compound or salt thereof according to (28), wherein the fatty acid has 2 to 16 carbon atoms.

(30) The compound or salt thereof according to (29), wherein the fatty acid is selected from the group consisting of lauric, acetic and octanoic acids.

(31) The $^{13}$C-labeled fluorescein ester compound or salt thereof according to (25), which is selected from the group consisting of the following compounds:
(a) $^{13}$C-dilaurylfluorescein;
(b) $^{13}$C-diacetylfluorescein; and
(c) $^{13}$C-dioctanoylfluorescein

(32) A diagnostic agent for pancreatic exocrine function comprising a $^{13}$C- or $^{14}$C-labeled fluorescein ester compound or a pharmaceutically acceptable salt thereof.

(33) The diagnostic agent for pancreatic exocrine function according to (32), comprising a compound or salt thereof resulting from a reaction of a $^{13}$C- or $^{14}$C-labeled acid with fluorescein at both or either of the two hydroxyl groups at 3' and 6' position to form an ester linkage.

(34) The diagnostic agent for pancreatic exocrine function according to (33), wherein the acid is a carboxylic acid.

(35) The diagnostic agent for pancreatic exocrine function according to (34), wherein the carboxylic acid is a fatty acid.

(36) The diagnostic agent for pancreatic exocrine function according to (35), wherein the fatty acid has 2 to 16 carbon atoms.

(37) The diagnostic agent for pancreatic exocrine function according to (32), which is selected from the group consisting of the following compounds:
(a) $^{13}$C-dilaurylfluorescein;
(b) $^{13}$C-diacetylfluorescein; and
(c) $^{13}$C-dioctanoylfluorescein.

(38) The diagnostic agent for pancreatic exocrine function according to any one of (32) to (37), wherein the $^{13}$C- or $^{14}$C-labeled fluorescein ester compound or pharmaceutically acceptable salt thereof is subjected to the action of the pancreatic exocrine cholesterol ester hydrolase and pancreatic exocrine esterase and decarboxylated to generate $^{13}CO_2$ or $^{14}CO_2$.

(39) A $^{13}$C-labelled oligosaccharide or polysaccharide or salt thereof according to any one of claims (1) to (10) for use in a method of diagnosis.

(40) Art inclusion complex according to any of claims (11) to 15 for use iii a method of diagnosis.

(41) A $^{13}$C or $^{14}$C-labelled fluorescein ester compound or salt thereof according to any one of claims (25) to (31) for use in a method of diagnosis.

(42) A compound according to any one of claims (39) to (41) wherein the diagnosis is the diagnosis of pancreatic exocrine function.

The term "oligosaccharide" refers to a sugar having two to ten or more monosaccharides polmerized. These monosaccharides may be modified.

The term "polysaccharide" refers to a sugar having monosaccharides polmerized at a degree of polymerization of at least 10. These monosaccharides may be modified.

The term "linear oligosaccharide or polysaccharide" refers to an oligosaccharide or polysaccharide having a linear chain structure such as maltooligosaccharides (e.g., maltotriose, maltotetraose, etc.) and polysaccharides (e.g., amylose, etc.).

The term "branched oligosaccharide or polysaccharide" refers to an oligosaccharide or polysaccharide having a branched structure such as amylopectin and glycogen.

The term "cyclic oligosaccharide or polysaccharide" refers to an oligosaccharide or polysaccharide having a cyclic structure such as cyclodextrin.

The term "non-reducing terminal" refers to the terminal at the side at which the carbon atom at position 1 of a sugar residue is involved in binding of the sugar chain.

This specification includes part or all of the contents as disclosed in the specifications and/or drawings of Japanese Patent Application Nos. 10-2712152, 10-271253, 11-261979 and 11-263300 which are priority documents of the present application.

DESCRIPTION OF THE INVENTION

Figure 1:
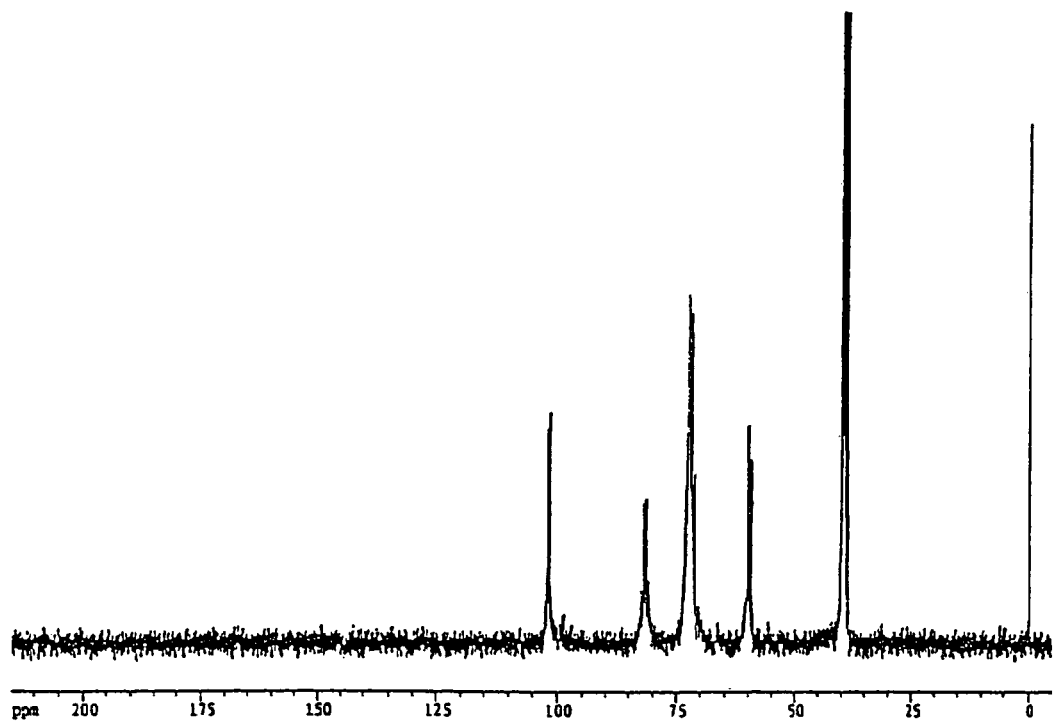
FIG. 1 shows a $^{13}$C-NMR spectrum of $^{13}$C-cyclodextrin.

Hereinafter, the present invention will be described in detail.

The present invention encompasses $^{13}$C-labeled oligosaccharide or polysaccharides or salts thereof, or derivatives thereof or $^{13}$C-labeled inclusion complex other than U-$^{13}$C-maltose, $^{13}$C-starch, 1-$^{13}$C-maltotetraose and 1-$^{13}$C-amylose. The diagnostic agent for pancreatic exocrine function of the present invention comprises a or $^{13}$C-labeled oligosaccharide or polysaccharide or a salt thereof a derivative thereof other than $^{13}$C-starch, or a $^{13}$C- or $^{14}$C-labeled inclusion complex or a salt thereof. Preferably, the $^{13}$C- or $^{14}$C-labeled oligosaccharide or polysaccharides or salts thereof, or derivatives thereof are modified at the non-reducing terminals or have cyclic structure. These $^{13}$C- or $^{14}$C-labeled compounds may be pharmaceutically acceptable.

The term "$^{13}$C- or $^{14}$C-labeled" herein means that carbon atom in the compound is replaced with a $^{13}$C or $^{14}$C atom, resulting in a higher abundance ratio of $^{13}C$ or $^{14}C$ than the naturally occuring abundance ratio irrespective of the preparation method thereof.

The "oligosaccharide or polysaccharides modified at their non-reducing terminals" refers to oligosaccharide or polysaccharides in which the carbon atom on their non-reducing terminal glucosyl group is modified. Modifying groups in addition to glucopyranose include modifying groups comprising oligosaccharides such as galactosyl and digalactosyl groups, alkyl groups, alkoxyl groups such as methoxy and benzyloxy groups, carbamoyl group, pyridylamino group, and ethylidene and benzylidene groups which are attached to two carbon atoms on the non-reducing terminal glucosyl group.

Examples of the oligosaccharide or polysaccharide or salt thereof, or derivative thereof include paranitrophenyl-6-o-benzyl maltopentaoside, 4-nitrophenyl maltohexaoside 4,6-ethylidene glucoside, 4,6-benzylidene α-o-4-nitrophenyl-maltopentaoside, o-6-deoxypyridylamino-α-maltopentaoside and paranitrophenyl-4,6-di-o-(N-ethyl)4-carbamoyl maltopentaoside and so on.

These compounds can be prepared by methods described in the following literature:
Carbohydrate Research, 176 (1988), 107-115;
Japanese Patent Application Laying Open No. 3-91496;
U.S. Pat. No. 4,649,108;
Journal of chromatography, 336 (1984), 368-373; and
Japanese Patent Application Laying Open No. 8-291

In the preparation, a $^{13}C$- or $^{14}C$-labeled maltooligosaccharide (which may be commercially available or be prepared by a known method) can be used as a starting material to give a $^{13}C$- or $^{14}C$-labeled one.

For example galactosyl oligosaccharide, which is an oligosaccharide modified at the non-reducing terminal, may be obtained by adding lactose to an oligosaccharide to bring lactase into action thereon, and collecting from the reaction mixture by column chromatography (Japanese Patent Application Laying Open Nos. 4-209277, 8-196289 and 10-316697). In the preparation, a $^{13}C$- or $^{14}C$-labeled oligosaccharide can be used to give a $^{13}C$- or $^{14}C$-labeled galactosyl oligosaccharide. When a $^{13}C$- or $^{14}C$-galactosyl labeled lactose is used, an galactosyloligosaccharide in which the galactosyl group is $^{13}C$- or $^{14}C$-labeled is obtained.

"Cyclodextrins" herein means α-1,4 linked cyclic oligosaccharides composed of glucopyranose units. The number of glucoses forming the ring is not limited at all and α-, β- and γ-cyclodextrins having 6 to 8 glucoses are commercially available. The cyclodextrin may have a branch. The hydroxyl group(s) in cyclodextrin may be modified; cyclodextrins having such a modifying group are included in the "modified derivatives of cyclodextrin". Illustratively, the modification includes alkylation such as methylation, hydroxyalkylation such as hydroxypropylation, esterification such as acetylation or succinylation, glucosylation, carboxymethyl etherification, phosphoric esterification, sulfobutyl etherification, and carboxymethylation. These modified derivatives are described in Loftsson et al., J. Pharmaceu. Sci., 85:1017 (1996); Stella et al., Pharmaceutical Res., 14:556 (1997); and "Cyclodextrins" supervised by Fujio Toda, published by Sangyo Tosho.

For example, a $^{13}C$- or $^{14}C$-labeled cyclodextrin may be obtained by bringing a cyclomaltodextrin glucanotransferase into action on a naturally occurring $^{13}C$-enriched starch derived from C4 plants such as corn or a commercially available $^{13}C$- or $^{14}C$-labeled starch and collecting from the reaction mixture by column chromatography.

Furthermore, a precipitation of $^{13}C$- or $^{14}C$-labeled β- and γ-cyclodextrin can be obtained by adding bromobenzene to a mixed solution of $^{13}C$- or $^{14}C$-labeled cyclodextrin, stirring the mixture at 10° C. overnight and subjecting it to centrifugation. This precipitation is washed with bromobenzene-saturated ice water, concentrated by vapor evaporation and left to stand, resulting in $^{13}C$- or $^{14}C$-labeled β-cyclodextrin. The mother liquor is treated with glucoamylase and mixed with cyclohexane. The supernatant is concentrated and mixed with n-propanol to give $^{13}C$- or $^{14}C$-labeled cyclodextrin.

A modified derivative of a cyclodextrin may be prepared in the following manner. For example, potassium hydroxide is added to an aqueous solution of β-cyclodextrin to make it alkaline and the solution is heated to 70 to 80° C. 2-Chloroethanol or 3-chloropropanol is then added. The mixture is then cooled to room temperature and neutralized and active carbon is added and filtered. The filtrate is concentrated and dried. DMF is added to the residue and insolubles are removed. Addition of acetone yields hydroxyethyl- or hydroxypropylcyclodextrin: Irie et al., Pharmaceutical Res., 5:713 (1988). In the preparation, a $^{13}C$- or $^{13}C$-labeled cyclodextrin can be used to give $^{13}C$- or $^{14}C$-labeled hydroxyethyl cyclodextrin or hydroxypropyl cyclodextrin.

The "cyclodextrin inclusion complex" refers to a cyclodextrin or a modified derivative thereof having any compound included in the cavity in the cyclic molecule. The compound included may be amino acids, fatty acids, organic acids, catechins, vitamins, carotenoids, flavonoids, cholesterols, and modified derivatives thereof. Additional examples of the compound included are oligosaccharides, peptides, fatty acid glycerides and modified derivatives thereof.

The $^{13}C$- or $^{14}C$-labeled cyclodextrin inclusion complex may be one in which any carbon atom in the included compound is replaced with a $^{13}C$ or $^{14}C$ atom, resulting in a higher abundance ratio of $^{13}C$ or $^{14}C$ in the cyclodektrin inclusion complex than the naturally occuring abundance ratio. However, the cyclodextrin or modified derivative thereof per se may be $^{13}C$- or $^{14}C$-labeled. Methods for the preparation thereof are not limited.

Examples of cyclodextrin inclusion complexes reported heretofore include the following (host molecules are not limited to ones indicated in the complexes):
Phenylalanine/β-cyclodextrin inclusion complex
Tryptophan/α-cyclodextrin inclusion complex
Histidine/α-cyclodextrin inclusion complex
Cinnalidine/β-cyclodextrin inclusion complex
Ferulic acid/β-cyclodextrin inclusion complex
Phenylalanyl leucine/β-cyclodextrin inclusion complex Other guest molecules include phenol, hydroxy benzoic acid, benzaldehyde, methyl sulfoxide, benzoic acid, aniline, amino benzoic acid, methyl benzoic acid, nitrophenol, pyridine, acetic acid, alcohols (e.g., ethanol, propanol, butanediol, etc.), prostandin, benexate hydrocholoride, nitroglycerin, limaprost and the like, which are described in "Cyclodextrin" edited by Fujio Toda, Sangyo Tosho. The cyclodextrin inclusion complex can be obtained by mixing purified water with a mixture of a host compound and a guest compound at a ratio equal to that of the host to the guest in the inclusion complex (e.g., at an equivalent molar ratio in the case where the ratio of the host to the guest is 1:1), stirring the resulting mixture for about 12 hours, and subjecting it to a spray dry treatment.

The $^{13}C$- or $^{14}C$-labeled oligosaccharide or polysaccharide or cyclodextrin inclusion complex may be also obtained in the form of a salt. Such salts include those with inorganic acids such as hydrochloric, sulfuric and phosphoric acids; those with organic acids such as formic, acetic, propionic, glycolic, succinic, malic, tartaric, citric and trifluoroacetic acids; those with alkali metals such as sodium and potassium; those with alkaline earth metals such as calcium; and those with ammonium or organic amines such as ethanolamine, triethylamine and dicyclohexylamine.

The present invention also encompasses $^{13}$C- or $^{14}$C-labeled fluorescein ester compounds or salts thereof.

Fluorescein (CA Name: 3',6'-dihydroxyspiro[isobenzofuran-1(3H),9'-[9H]xanthen-3-one) is represented by the following structural formula:

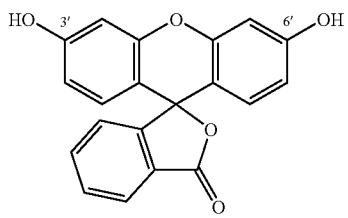

The "fluorescein ester compound" refers to a compound resulting from a reaction of an acid with fluorescein at the hydroxyl group(s) to form an ester linkage. Fluorescein and the acid may be modified.

The "$^{13}$C- or $^{14}$C-labeled" means that at least one carbon atom in the fluorescein ester compound is replaced with a $^{13}$C- or atom, resulting in a higher abundance ratio of the $^{13}$C- or $^{14}$C atom than the naturally occuring abundance ratio.

In one embodiment of the present invention, the $^{13}$C- or $^{14}$C-labeled fluorescein ester compound or salt thereof is a compound resulting from a reaction of a $^{13}$C- or $^{14}$C-labeled acid with fluorescein or a salt thereof at both or either of the hydroxyl groups at 3' and 6' positions to form an ester linkage.

An example of the $^{13}$C- or $^{14}$C-labeled acid may be a carboxylic acid, preferably a fatty acid. The "fatty acid" herein refers to a compound represented by the formula R—COOH in which R is an aliphatic group which may optionally have a branch(es) and/or a double bond(s). The number of carbons in the fatty acid is preferably 2 to 16.

Examples of the fatty acid include acetic, octanoic and lauric acids but are not limited thereto.

Examples of the $^{13}$C- or $^{14}$C-labeled fluorescein ester compound include $^{13}$C-dilauryfluorescein, $^{13}$C-diacetylfluorescein, $^{13}$C-dioctanoylfluorescein, and the like.

The $^{13}$C- or $^{14}$C-labeled fluorescein ester compound may be prepared in the following manner.

For example, fluorescein is dissolved in chloroform and an equal or twice molar amounts of a $^{13}$C- or $^{14}$C-labeled fatty acid chloride is added. Then, a chloroform solution containing pyridine is dropwise added and stirred and heated under dark. After the reaction, the solvent is distilled out. Column chromatography and recrystallization yield the $^{13}$C- or $^{14}$C-labeled fluorescein ester compound.

The $^{13}$C- or $^{14}$C-labeled fluorescein ester compound may be prepared in the form of a salt. The salts may include sodium and potassium salts.

The diagnostic agent for pancreatic exocrine function according to the present invention may be formulated from the $^{13}$C- or $^{14}$C-labeled compound alone or in combination with an excipient or carrier into an oral preparation such as a tablet, capsule, powder, granule or liquid. The excipient or carrier may be any pharmaceutically acceptable one ordinarily used in this field and its nature and composition may be appropriately chosen. For example, water may be used as a liquid carrier. Solid carriers include cellulose derivatives such as hydroxypropyl cellulose, and organic acid salts such as magnesium stearate. Also, freeze-dried preparations may be used.

The $^{13}$C- or $^{14}$C-labeled compound is contained in the preparation in variable amounts depending on the nature of the preparation, but generally in an amount of 1 to 100% by weight, preferably 50 to 100% by weight. In a capsule, tablet, granule or powder preparation, the $^{13}$C- or $^{14}$C-labeled compound is contained in the preparation in an amount of about 10 to 100% by weight, preferably 50 to 100% by weight, the balance being a carrier.

The dose of the diagnostic agent for pancreatic exocrine function according to the present invention should be sufficient to confirm an increase of $^{13}$CO$_2$ or $^{14}$CO$_2$ in the breath after the administration. It will vary depending upon the age and body weight of a subject and the purpose of the test. For example, the unit dose may be 1 to 2000 mg/kg of body weight for an adult.

The test using the agent for pancreatic exocrine function according to the present invention is carried out with administering to a subject the $^{13}$C- or $^{14}$C-labeled compound. A test is possible, in which the concentration of a or $^{13}$C- or $^{14}$C-labeled compound is measured in serum, urine or stool after the administration, however, a breath test is desirable in which an increase in $^{13}$C or $^{14}$C concentration is measured in the exhaled CO$_2$ after the administration. When the $^{13}$C- or $^{14}$C-labeled compound is administered to a subject, a test meal or the like may be pre-ingested by the subject to induce secretion of pancreatic enzymes. The $^{13}$C- or $^{14}$C-labeled compound may be administered together with the test meal or the like. Also, a plurality of the $^{13}$C- or $^{14}$C-labeled compound may be combined for use. Concretely, in the case of $^{13}$C, the $^{13}$C concentration is determined in the exhaled CO$_2$ after the administration, then the pancreatic exocrine function is diagnosed from either the data of the degree of increase ($\Delta^{13}$C ((‰))) of the $^{13}$C concentration in the exhaled CO$_2$ at predetermined times (e.g., 5, 10 and 15 minutes) after the administration, or the data integrated or associated with the time course (onset slope, change in slope, peak time, etc.) in the degree of increase ($\Delta^{13}$C (‰)) of the $^{13}$C concentration in the exhaled CO$_2$ during a predetermined period after the administration. In the case of $^{14}$C, the $^{14}$C concentration, i.e., radioactivity, is determined in the exhaled CO$_2$ after the administration; and the pancreatic exocrine function is diagnosed from either the data of the quantity of radioactivity in the exhaled CO$_2$ at predetermined times (e.g., 5, 10 and 15 minutes) after the administration, or the data integrated or associated with the time course (onset slope, change in slope, peak time, etc.) in the rate increase of radioactivity in the exhaled CO$_2$ during a predetermined period after the administration.

These test methods utilize the phenomenon that when the $^{13}$C- or $^{14}$C-labeled compound is administered to a subject, the compound is absorbed through the digestive tract after it is degraded by the action of the pancreatic exocrine α-amylase, and/or esterase, and decarboxylated by metabolic action in the body to generate $^{13}$CO$_2$ or 4CO$_2$ which is excreted into the breath.

When a cyclodextrin inclusion complex, in which an oligosaccharide, peptide, fatty acid glyceride or a modified derivative thereof is included, is used, the first reaction of the degradation is the cleavage of the cyclodextrin by α-amylase and the oligosaccharide, peptide, fatty acid glyceride or modified derivative thereof released in association with the cleavage is then degraded by the action of the pancreatic exocrine α-amylase, protease, lipase or the like to be absorbed through the digestive tract and decarboxylated by metabolic action in the body to generate $^{13}CO_2$ or $^{14}CO_2$ which is excreted into the breath.

The $^{13}C$ concentration in the exhaled $CO_2$ can be determined by gas chromatography-mass spectrometry (GC-MS), infrared spectroscopy, mass spectromecry, photoelectric acoustic spectroscopy, NMR (nuclear magnetic resonance), and other methods.

The $^{14}C$ concentration or radioactivity in the exhaled $CO_2$ may be measured from the breath of a subject, directly or after trapping $CO_2$ in a solvent, with a GM counter, a liquid scintillation counter, a solid scintillation counter, autoradiography, an ionization chamber, or the like.

The diagnostic agent for pancreatic exocrine function according to the present invention is particularly effective in the diagnosis of the α-amylase and/or esterase secretion ability of the pancreas.

Hereinbelow, the present invention is illustrated in more detail by the following examples; however, the scope of the present invention shall not be limited by the example.

EXAMPLES

Example 1

Preparation of $^{13}C$-Labeled cyclodextrin $^{13}C$-labeled starch (Chlorella Industry, Algal Starch (water-soluble), Lot No. 8031,S, U-$^{13}C$:98.6 atom %, Starch Content: 93.5%) was dissolved in 50 mM acetate buffer (pH 5.4) at a concentration of 5% (w/v) and 100 Units of cyclomaltodextrin glucanotransferase (Hayashibara) was added thereto and reacted at 40° C. for 24 hours. After the enzyme was inactivated with the treatment at loot for 15 minutes, glucoamylase was added and reacted at 40° C. for 1 hour to decompose components other than $^{13}C$-labeled cyclodextrin into glucose. After the reaction was completed, the reaction mixture was treated at 100° C. for 15 minutes to inactivate the glucoamylase.

The solution was applied to a carbon column (2.5 cm×25 cm) and the column was washed with 500 ml of water. A 15% ethanol solution and a 40% ethanol solution were sequentially applied to recover the $^{13}C$-labeled cyclodextrin in the 40% ethanol solution eluted fractions. The resulting $^{13}C$-labeled cyclodextrin solution was distilled to remove the solvent, dissolved in a small amount of water and freeze-dried.

The product was mixed with para-nitrophenol to confirm to be cyclodextrin from an increase in absorbance at a wave length of 450 nm.

The $^{13}C$-labeled position was confirmed by $^{13}C$-NMR (FIG. 1).

$^{13}C$-NMR (DMSO-d6,300 MHz)
38.5-40.2 ppm Dimethyl sulfoxide
595-60.1 ppm Position 6 of glucose residue
71.4-73.1 ppm Positions 3, 4 and 5 of glucose residue
80.9-82.5 ppm Position 2 of glucose residue
101.5-102.1 ppm Position 1 of glucose residue HPLC analysis (Shodex Asahipak GS-220 HQ) of the resulting $^{13}C$-labeled cyclodextrin revealed that it was a mixture of 45% of α-cyclodextrin, 45% of γ-cyclodextrin and 10% of γ-cyclodextrin.

Example 2

$^{13}C$-Labeled cyclodextrin Breath Test $^{13}C$-labeled cyclodextrin breath test was carried out wherein $^{13}C$-labeled cyclodextrin prepared in Example 1 was orally administered to chronic pancreatitis and control rats and the time course of the $^{13}C$ concentration in the exhaled $CO_2$ after the administration was measured.

According to Mundlos et al. (Mundlos et al., Pancreas, 1:29 (1986)), the chronic pancreatitis rats were prepared by injecting oleic acid into the pancreatic duct of Wistar male rats of 5 weeks old and kept for 3 weeks. Rats in which midline incision was made on the abdomen were used as the control.

The chronic pancreatitis and control rats of 8 weeks old, which fasted overnight, were fixed without anesthesia in a rat holder for a microwave irradiation apparatus. The breath was collected at a rate of about 100 to 300 ml/min using a stroke pump (Variable Stroke Pump VS-500, Shibata Kagaku Kogyo) and introduced directly to a flow cell of a $^{13}CO_2$ analyzer EX-130S (Nihon Bunko) to measure $^{13}C$ atom % and the carbon dioxide gas concentration continuously. A Perma Pure drier (MD-050-12P, Perma Pure Inc.) was set between the rat holder and the stroke pump to remove out water vapor in the breath. After the $CO_2$ concentration was stabilized, the rat was once removed out of the rat holder and an aqueous solution of $^{13}C$-labeled cyclodextrin was administered (75 mg/kg, 5 ml/kg) into the stomach using an oral sonde.

$\Delta^{13}C$ (‰) was calculated from the $^{13}C$ concentration in the exhaled $CO_2$ at each time point ($^{13}C$ tmin) and the $^{13}C$ concentration in standard $CO_2$ ($^{13}C$ std) according to the following equation:

$$\Delta^{13}C\ (‰)=[(^{13}C\ tmin-^{13}C\ 0\ min)/^{13}C\ std]\times 1000$$

Figure 2:
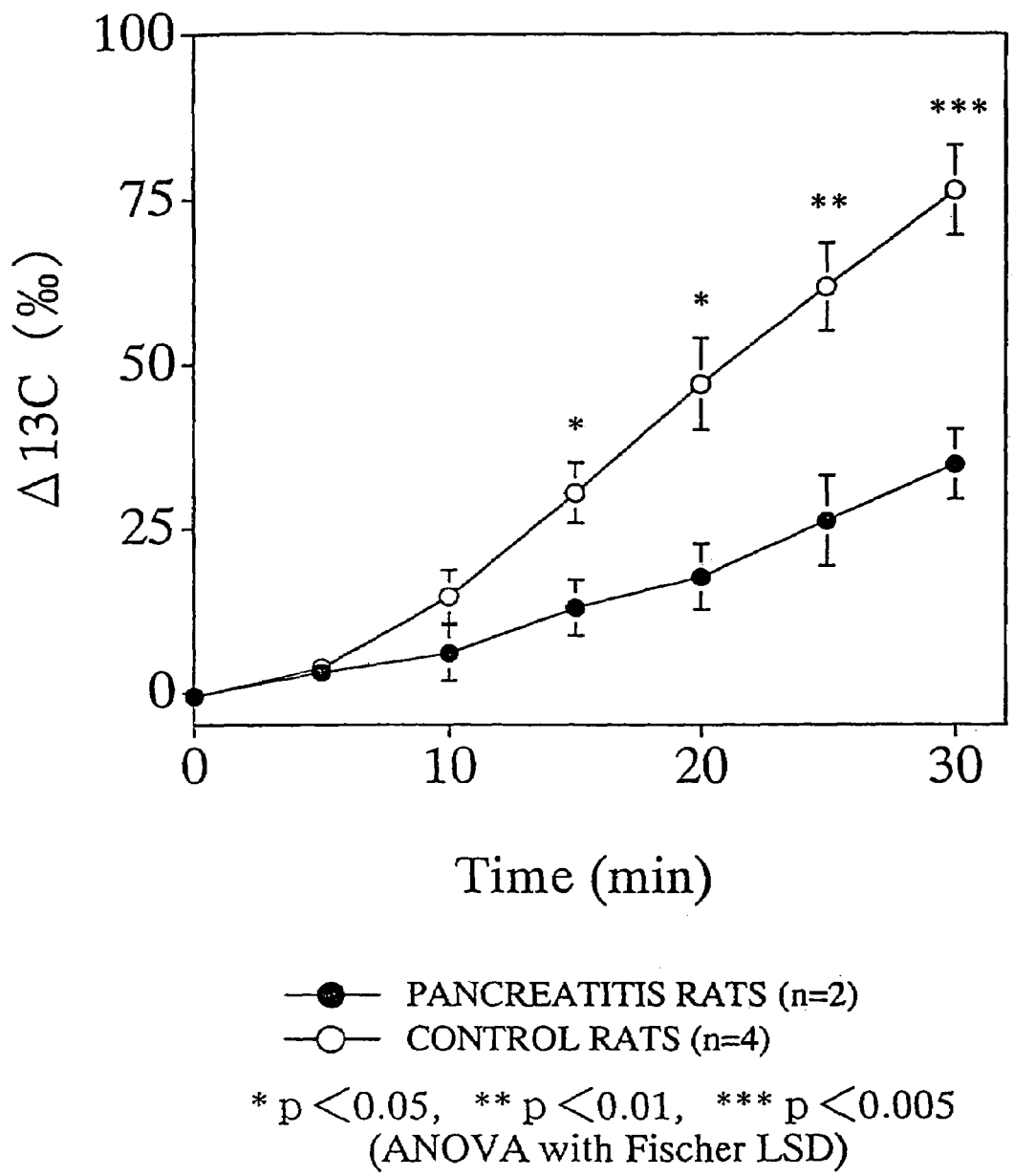
FIG. 2 shows the time course of degree of increase of the $^{13}$C concentration in the exhaled $CO_2$ ($\Delta^{13}C$ (‰)) after administration of $^{13}$C-labeled cyclodextrin. At 0 minutes, $^{13}$C-labeled cyclodextrin was orally administered (75 mg/kg) to chronic pancreatitis rats (n=2, M) and control rats (n=4, F). The bar indicates SD.

In both the control and chronic pancreatitis rats, the $\Delta^{13}C$ (‰) values continued to increase for 30 minutes. However, the increase in $\Delta^{13}C$ (‰) value of the chronic pancreatitis rats was smaller than the control rats (FIG. 2). At 15 minutes, the $\Delta^{13}C$ (‰) value of 12.88±4.25 in the chronic pancreatitis rats was significantly smaller than the value of 30.39±5.29 in the control rats (p<0.05, ANOVA with Fischer LSD).

Example 3

Preparation of $^{13}C$-Labeled galactosylmaltohexaose $^{13}C$-labeled starch (Chlorella Industry, 4.65 g) was dissolved in a 50 mM acetate buffer (pH 5.4) at a concentration of 0.5% (w/v) and 186 Units of cyclomaltodextrin glucanotransferase (Hayashibara) was added thereto and reacted at 40° C. for 2 hours and 20 minutes. The enzyme was inactivated with the treatment at 95° C. for 15 minutes and the product was purified by Sephadex G-25. This procedure was repeated 4 times to yield 4.39 g of $^{13}C$-α-cyclodextrin (yield 23.6%).

Pyridine (200 mL) was added to 4.39 g of the resulting $^{13}C$-α-cyclodextrin and ice cooled. Acetic anhydride (100 mL) was added thereto. After 30 minutes, the reaction mixture was removed out of the ice bath and then stirred at room temperature for 36 hours. To the residue obtained by concentration under reduced pressure, toluene was added and azeotropically distilled. This procedure was repeated three times. Ethyl acetate and water were added to the residue to extract. The organic layers were combined, dried over anhydrous magnesium sulfate and filtered and the filtrate was concentrated under reduced pressure. The resulting residue was purified by silica gel column chromatography to yield 5.1 g of peracetylated $^{13}C$-α-cyclodextrin.

The peracetylated $^{13}C$-α-cyclodextrin (3.25 g) was dissolved in acetic anhydride (49.8 mL) and sulfuric acid (1.02 mL) and stirred under heating at 55° C. After 5 hours, the reaction mixture was ice cooled and pyridine (5.1 mL) was added. The reaction mixture was concentrated under reduced pressure and toluene was added to the resulting residue. This procedure was repeated three times. Chloroform and water were added to the residue to extract. The organic layers were combined, dried over anhydrous magnesium sulfate and filtered and the filtrate was concentrated under reduced pressure. The resulting residue was purified by silica gel column chromatography. This procedure was repeated twice and the collected starting material was again used in the ring-opening reaction to yield 4.80 g of peracetylated $^{13}C$-maltohexaose from 6.50 g in total of the starting material.

The peracetylated $^{13}C$-maltohexaose (3.76 g) was dissolved in 1500 mL of dry methanol and ice cooled. A solution of 5.18 M sodium methoxide in methanol (776 Φ1) was added thereto. After 30 minutes, the reaction mixture was returned to room temperature and stirred. After 20 hours, a solution of 5.18 M sodium methoxide in methanol (388 Φ1) was added. After 3.5 hours, Amberlyst 15 (16 g) was added to neutralize and filtered. The resin was washed with methanol and water and the filtrate and washings were combined and concentrated under reduced pressure. The resulting residue was purified by HPLC (TSK-Gel Amide-80 column) to yield 1.78 g of $^{13}C$-maltohexaose. The same procedure was repeated twice to yield 2.03 g of $^{13}C$-maltohexaose in total.

To 2.03 g of $^{13}C$-maltohexaose and 710 mg of lactose monohydrate, 20 mM potassium phosphate buffer (pH 7.0, 6.50 mL) was added and dissolved at 40° C. A solution of Biolacta (lactase) (Daiwa Kasei, 0.87 mg) in 20 mM potassium phosphate buffer (20 Φ1) was added and allowed to stand at 40° C. After 9.5 hours, the reaction mixture was heated at 95° C. for 15 minutes. The enzymic reaction solution was purified by HPLC (TSK-Gel Amide-80 column) to yield 239 mg of galactosyl $^{13}C$-maltohexaose. HPLC analysis (TSK-Gel Amide-80 column) of the pyridylaminated galactosyl $^{13}C$-maltohexaose revealed that the resulting galactosyl $^{13}C$-maltohexaose comprised β-1,4-galactosyl $^{13}C$-maltohexaose as a main component and not more than 9% of β-1,6-galactosyl $^{13}C$-maltohexaose.

Figure 3:
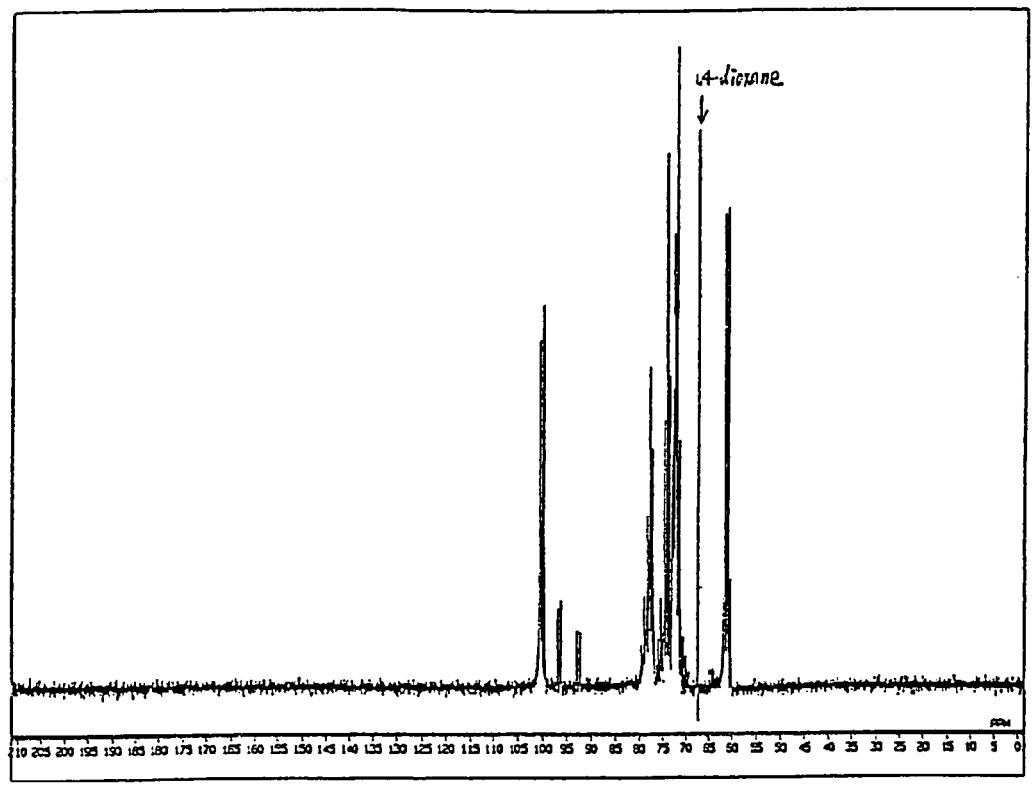
FIG. 3 shows a $^{13}$C-NMR spectrum of galactosyl $^{13}$C-maltohexaose.

The structure was confirmed by $^{13}C$-NMR (FIG. 3) and mass spectrometry. $^{13}C$-NMR ($D_2O$, 270 MHz) 60.3-61.6 ppm Position 6 of 6 glucose residues 67.4 ppm 1,4-Dioxane 70.7-79.6 ppm Positions 2, 3, 4 and 5 of 6 glucose residues 92.4-96.9 ppm Position 1 of the reducing terminal glucose 100.1-101.5 ppm Position 1 of 5 glucose residues Mass spectrometry (ESI-MS) m/z: 1211.3 ($M^+$+Na)

Example 4

Galactosyl $^{13}C$-Labeled inaltohexaose Breath Test

As in Example 2, a galactosyl $^{13}C$-labeled maltohexaose breath test was carried out wherein galactosyl $^{13}C$-labeled maltohexaose obtained in Example 3 was orally administered (75 mg/kg) to chronic pancreatitis and control rats and the time course of the $^{13}C$ concentration in the exhaled $CO_2$ after the administration was measured.

Figure 4:
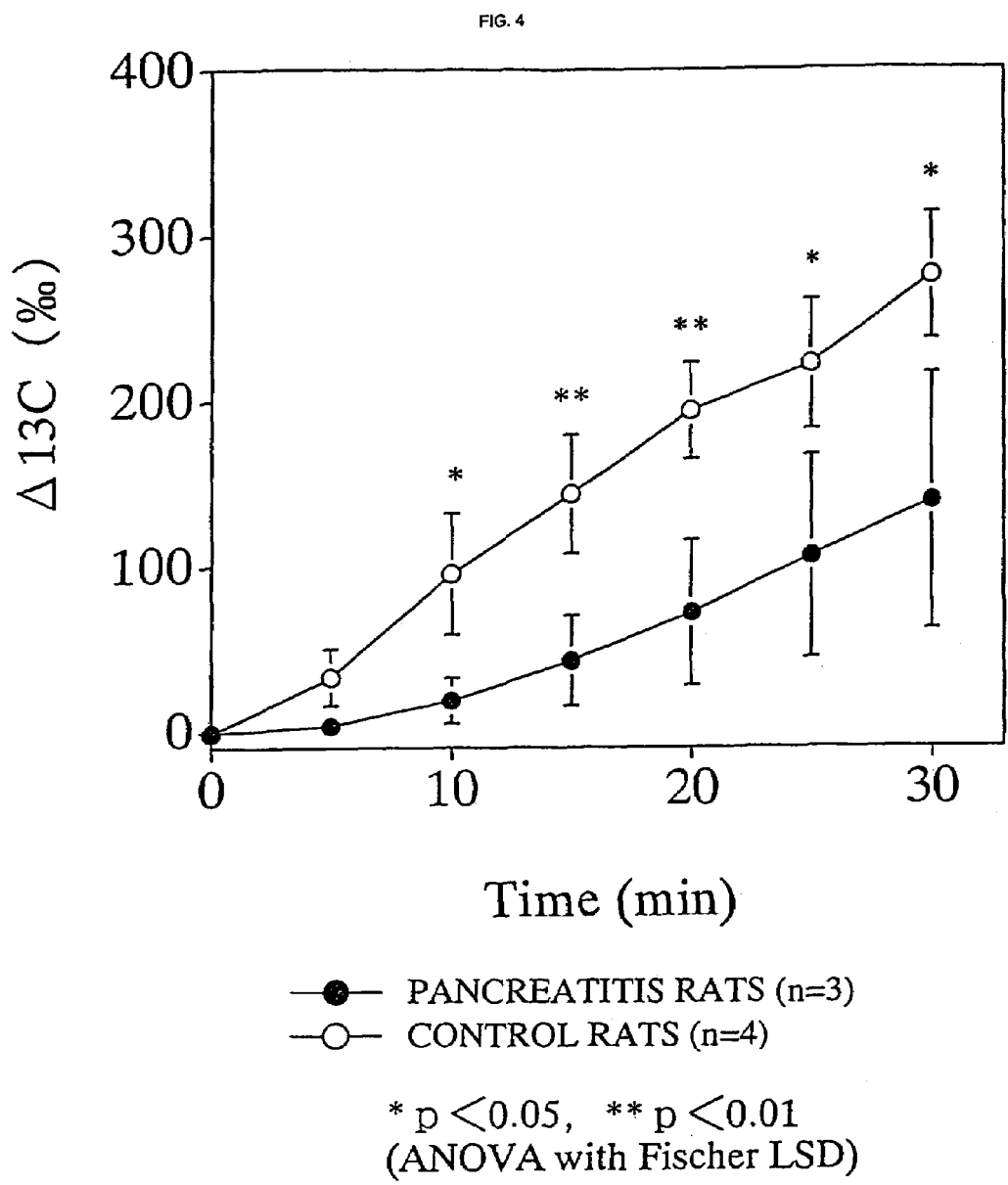
FIG. 4 shows the time course of degree of increase of the $^{13}$C concentration in the exhaled $CO_2$ ($\Delta^{13}C$ (‰)) after administration of $^{13}$C-galactosyl maltohexaose. At 0 minutes, $^{13}$C-galactosyl maltohexaose was orally administered (75 mg/kg) to chronic pancreatitis rats (n=3, M) and control rats (n=4, F). The bar indicates SD.

In both the control and chronic pancreatitis rats, the $\Delta^{13}C$ (‰) values continued to increase for 30 minutes. However, the increase in $\Delta^{13}C$ (‰) value of the chronic pancreatitis rats was smaller than the control rats (FIG. 4). At 10 minutes after the administration, the $\Delta^{13}C$ (‰) value (18.89±17.01%) of in the chronic pancreatitis rats was significantly smaller than the value (95.57±42.40%) of in the control rats (p<0.05, ANOVA with Fischer LSD).

Example 5

Preparation of [1-$^{13}C$]-phenylalanine/hydroxypropyl-β-cyclodextrin Inclusion complex To 5 ml of distilled water, 299 mg of (1-$^{13}C$]-phenylalanine and 1818, mg hydroxypropyl-β-cyclodextrin (in a molar ratio of 1:1) were added and heated to 85° C. to make a solution. Thus, a solution of (1-$^{13}C$] phenylalanine/hydroxypropyl-β-cyclodextrin inclusion complex was prepared wherein when this solution was allowed to cool to 25° C., no precipitation of phenylalanine was observed while the solubility of phenylalanine is 148 mg/5 ml at 25° C. On the other hand, if 299 mg of (1-$^{13}C$]-phenylalanine only was added to 5 ml of distilled water and heated to 85° C. to dissolve, phenylalanine was precipitated when this solution was allowed to cool to 25° C. The increase of solubility of phenylalanine in the presence of hydroxypropyl-β-cyclodextrin confirmed the formation of (1-$^{13}C$]-phenylalanine/hydroxypropyl-β-cyclodextrin inclusion complex.

Example 6

[1-$^{13}C$]-phenylalanine/hydroxypropyl-β-cyclodextrin Inclusion Complex Breath Test As in Example 2, a [1-$^{13}C$]-phenylalanine/hydroxypropyl-β-cyclodextrin inclusion complex breath test was carried out wherein [1-$^{13}C$]-phenylalanine/hydroxypropyl-β-cyclodextrin inclusion complex obtained in Example 5 was orally administered (59.76 mg/kg of [1-$^{13}C$]-phenylalanine) to chronic pancreatitis and control rats and the time course of the $^{13}C$ concentration in the exhaled $CO_2$ after the administration was measured.

The chronic pancreatitis rats were WBN/kob male rats (Japan SLC, Inc.) of 19 weeks old. The control rats were Wistar male rats of 19 weeks old.

Figure 5:
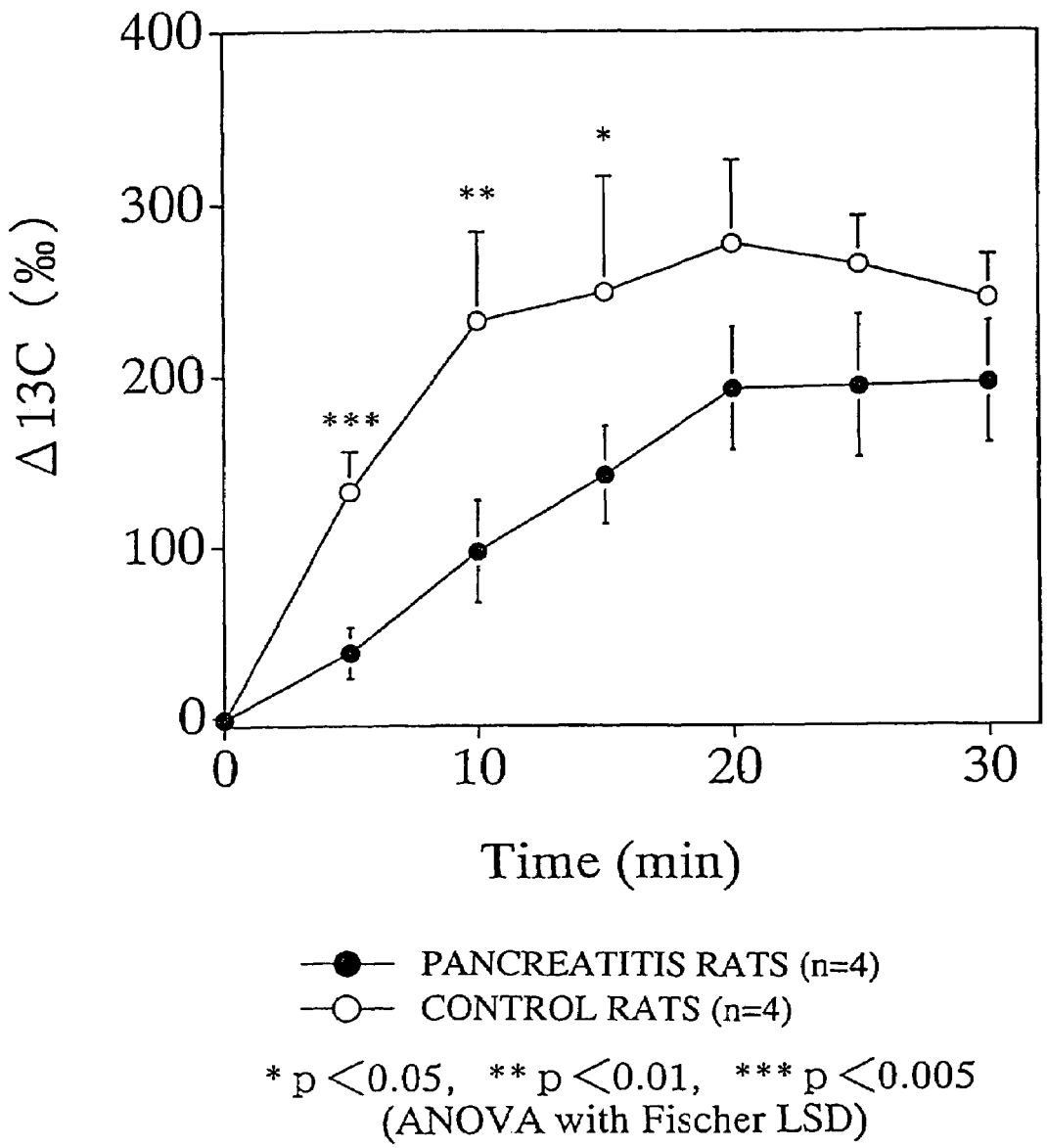
FIG. 5 shows the time course of degree of increase of the $^{13}$C concentration in the exhaled $CO_2$ ($\Delta^{13}C$ (‰)) after administration of $^{13}$C-labeled phenylalanine/hydroxypropyl-β-cyclodextrin (1-$^{13}$C-Phe/hp-β-CD) inclusion complex. At 0 minutes, 1-$^{13}$C-Phe/hp-β-CD inclusion complex was orally administered (59.76 mg/kg of 1-$^{13}$C-Phe) to chronic pancreatitis rats (n=4, M) and control rats (n=4, F). The bar indicates SD.

The $\Delta^{13}C$ (‰) values of the chronic pancreatitis rats were smaller than the control rats during 3.0 minutes (FIG. 5). At 5 minutes after the administration, the $\Delta^{13}C$ (‰) value of 38.18±17.46 in the chronic pancreatitis rats was significantly smaller than the value of 132.60±26.79 in the control rats (p<0.005, ANOVA with Fischer LSD).

Example 7

Preparation of benzoylphenylalanyl[1-$^{13}C$]-leucine/γ-cyclodextrin Inclusion Complex After 1 g of 1-$^{13}C$-L-leucine (Masstrace) was dissolved in hydrogen chloride/methanol and refluxed, the resulting $^{13}C$-L-leucine methyl ester was suspended in 50 ml of dichloromethane and 1.08 ml of triethylamine was added dropwise under while being ice-cooled and stirred. Further, 2.0 g of N-benzoyl-DL-phenylalanine, 2.34 g of HOBt (1-hydroxy-1H-benzotriazole $H_2O$) and 50 ml of dichloromethane were added. Then, a solution of 1.49 g of WSC (1-ethyl-3-(3-dimethylaminopropyl)-carbodiimide.HCL) dissolved in 100 ml of dichloromethane was added and stirred for 1 hour under while being ice-cooled and then overnight at room temperature. The completion of the reaction was confirmed by silica gel thin layer chromatography using chloroform: methanol (95:5) as a developing solvent. The reaction mixture was concentrated, extracted with ethyl acetate, washed with 1N-HCL, 5% $NaHCO_3$, and water, dried over magnesium sulfate, and concentrated to dryness to yield 2.32 g of benzoylphenylalanyl-[1-$^{13}$C]-leucine methyl ester.

After 2.32 g of benzoylphenylalanyl-[1-$^{13}$C]-leucine methyl ester was dissolved in 100 ml of methanol, 6.4 ml of 1N NaOH was added dropwise under while being ice-cooled and stirred followed by heating and stirring at 70° C. for 2.5 hours. The completion of the reaction was confirmed by silica gel thin layer chromatography using chloroform:methanol (95:5) as a developing solvent. After the reaction was completed, the reaction mixture was neutralized with 1N-HCl, concentrated and dissolved in 5% $NaHCO_3$. After washing with ethyl acetate, 5% $NaHCO_3$ was acidified with 1N-HCl. The reaction mixture was extracted with ethyl acetate, washed with water, dried over magnesium sulfate, and concentrated to dryness to yield 1.93 g of benzoylphenylalanyl-[1-$^{13}$C]-leucine, which was then recrystallized with ethyl acetate.

The structure and $^{13}$C-labeled position were confirmed by $^{13}$C-NMR and mass spectrometry. $^{13}$C-NMR (methanol-d4, 300 MHz): 175.8 ppm ($^{13}$COOH) Mass spectrometry (m/z): 383 ($M^+$), 365, 224, 131, 105, 77 LC-MS (m/z): 384 ($M^+$+H), 252, 224, 105 Benzoylphenylalanyl(1-$^{13}$C]-leucine was prepared so that the weight ratio thereof to γ-cyclodextrin was 1:4 (1:1 in molar ratio). γ-Cyclodextrin and benzoylphenylalanyl(1-$^{13}$C]-leucine were dissolved in a small amount of purified water and ethanol, respectively, and the both solutions were mixed together, stirred with a stirrer (500 rpm) for 12 hours, and then spray dried using Pulvis minispray GA-31 (Yamato Kagaku) under the conditions: an inlet temperature of 100° C., an outlet temperature of 50° C., a dry air flow rate of 0.45 $m^3$/min, a spray pressure of 1.5 kg/$cm^2$, and a flow rate of 5 ml/min. The resulting sample was further dried under reduced pressure for 24 hours and passed through No. 18 sieve (850 Φm). Thus, benzoylphenylalanyl(1-$^{13}$C]-leucine/γ-cyclodextrin inclusion complex was obtained as a powder remaining on No. 50 sieve (300 Φm)

Figure 6:
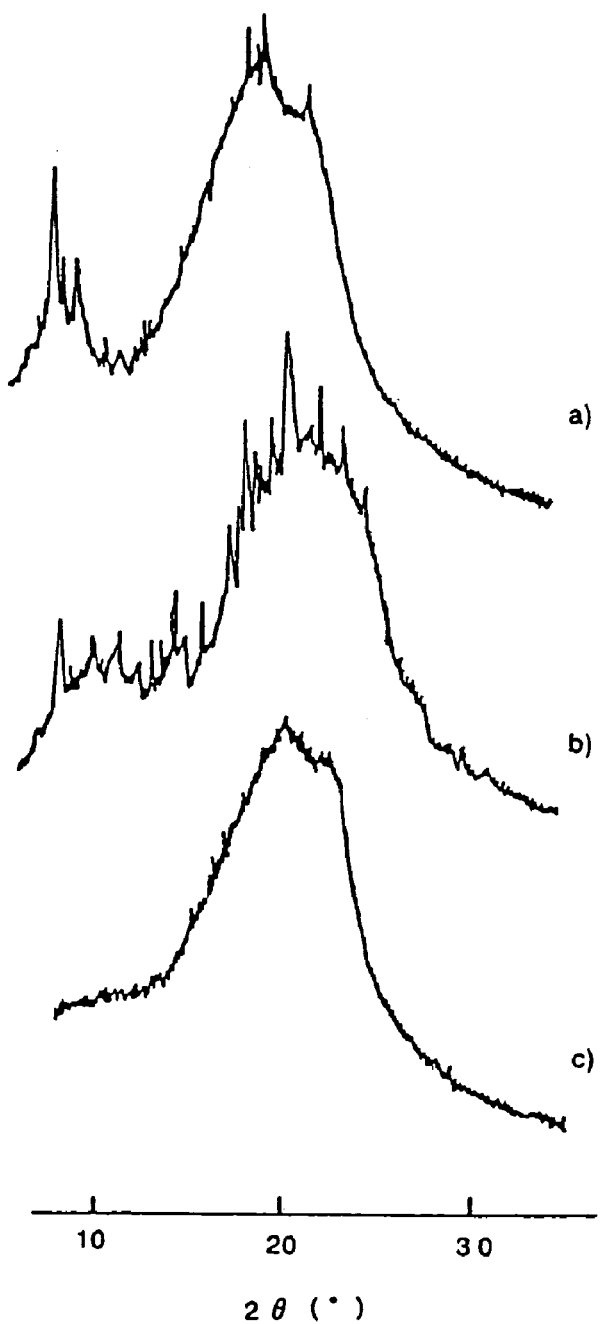
FIG. 6 is a powder X-ray diffraction spectrum of benzoylphenylalanyl[1-$^{13}$C]-leucine/γ-cyclodextrin (Bz-Phe-($^{13}$C-Leu)/γ-CD) inclusion complex.

The structure was confirmed by powder X-ray diffraction using Geigerflex Model 2013 diffractometer (Rigaku Denki) under the conditions: Ni filter, Cu-K α line (30 kV, 20 mA), a scanning speed of 1° /min. In the benzoylphenylalanyl[1-$^{13}$C]-leucine/γ-cyclodextrin inclusion complex, no diffraction peak inherent to benzoylphenylalanyl[1-$^{13}$C]-leucine or γ-cyclodextrin was observed but a halo curve was observed (FIG. 6).

Example 8

Benzoylphenylalanyl(1-$^{13}$C]-leucine/γ-cyclodextrin Inclusion Complex Breath Test As in Example 2, a benzoylphenylalanyl[1-$^{13}$C]-leucine/γ-cyclodextrin inclusion complex breath test was carried out wherein benzoylphenylalanyl[1-$^{13}$C]-leucine/γ-cyclodextrin inclusion complex obtained in Example 7 was orally administered (suspended in 0.5% sodium carboxymethyl cellulose (CMC-Na) solution, 100 mg/kg of benzoylphenylalanyl[1-$^{13}$C]-leucine) to chronic pancreatitis and control rats and the time course of the $^{13}$C concentration in the exhaled $CO_2$ after the administration was measured.

Figure 7:
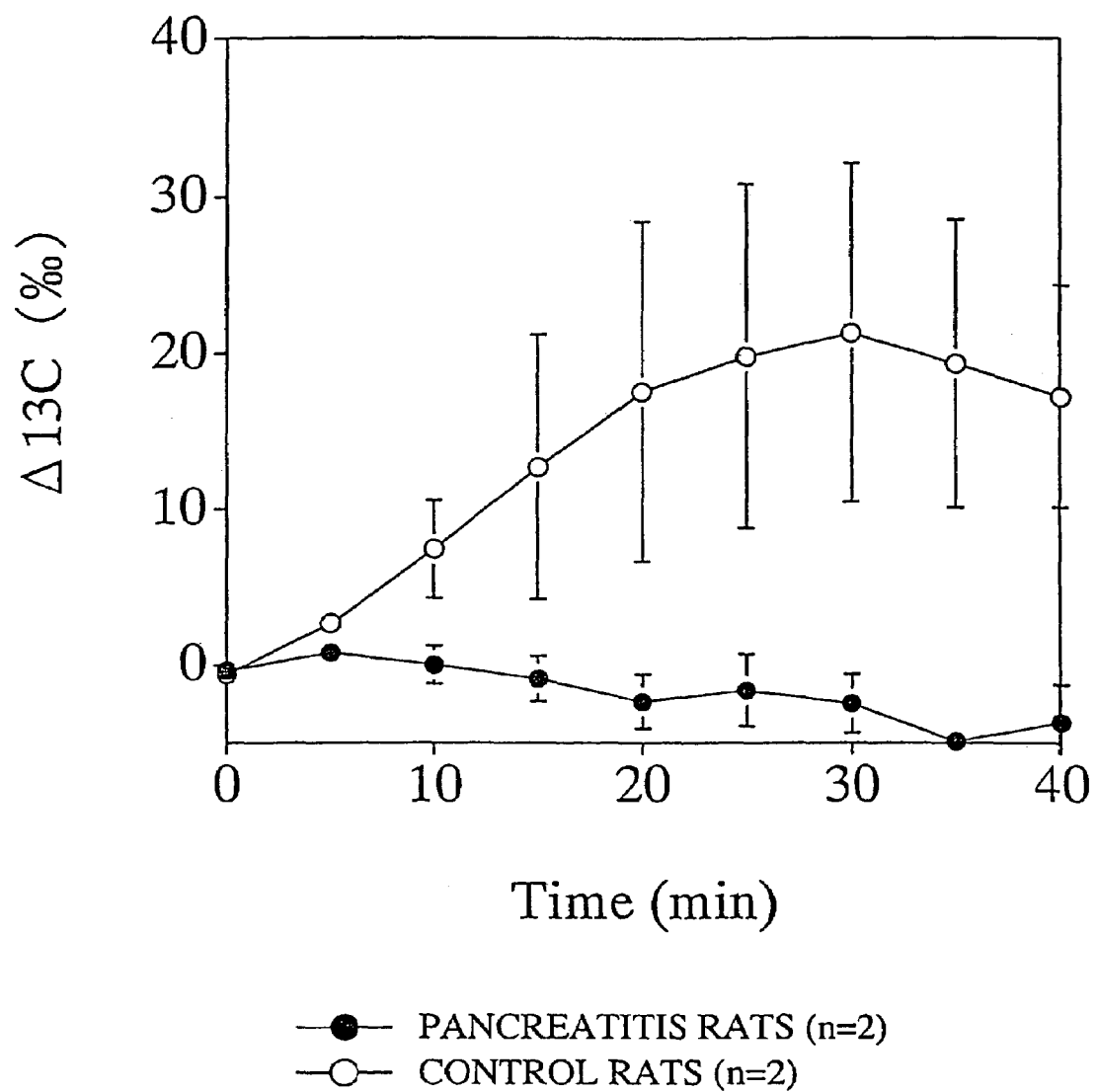
FIG. 7 shows the time course of degree of increase of the $^{13}$C concentration in the exhaled $CO_2$ ($\Delta^{13}C$ (‰)) after administration of benzoylphenylalanyl[1-$^{13}$C]-leucine/γ-cyclodextrin (Bz-Phe-($^{13}$C-Leu)/γ-CD) inclusion complex. At 0 minute, Bz-Phe-($^{13}$C-Leu)γ-CD was orally administered (100 mg/kg of Bz-Phe-($^{13}$C-Leu)) to chronic pancreatitis rats (n=2, M) and control rats (n=2, F). The bar indicates SD.

The $\Delta^{13}$C (‰) values of the chronic pancreatitis rats were smaller than the control rats during 40 minutes (FIG. 7). At 10 minutes after the administration, the $\Delta^{13}$C (‰) value of 0.03 ±1.73 in the chronic pancreatitis rats was smaller than the value of 7.43±4.42 in the control rats.

Example 9

Preparation of benzoylphenylalanyl[1-$^{13}$C]-leucine methyl ester/γ-cyclodextrin Inclusion Complex Benzoylphenylalanyl(1-$^{13}$C]-leucine methyl ester (prepared in Example 7) was prepared so that the weight ratio thereof to γ-cyclodextrin was 1:4 (1:1 in molar ratio). γ-Cyclodextrin and benzoylphenylalanyl [1-$^{13}$C]-leucine methyl ester were dissolved in a small amount of purified water and ethanol, respectively, and the both solutions were mixed together, and stirred with a stirrer (500-rpm) for 12 hours. Then, the procedures of Example 7 were repeated to yield benzoylphenylalanyl(1-$^{13}$C]-leucine methyl ester/γ-cyclodextrin inclusion complex.

Figure 8:
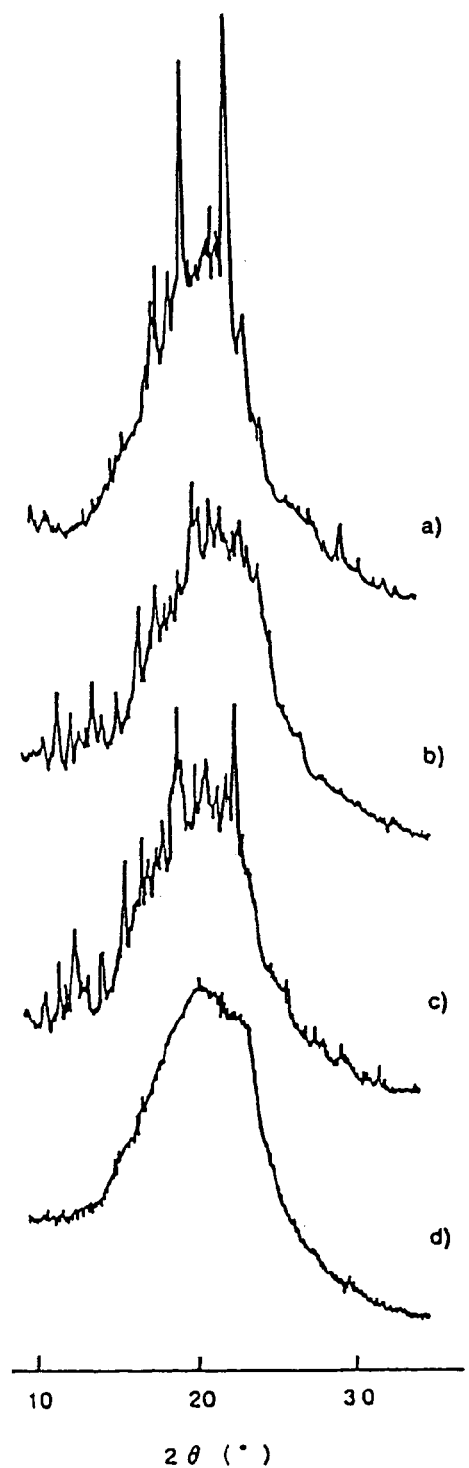
FIG. 8 is a powder X-ray diffraction spectrum of benzoylphenylalanyl[1-$^{13}$C]-leucine methyl ester/γ-cyclodextrin (Bz-Phe-($^{13}$C-Leu)Me/γ-CD) inclusion complex.

The structure was confirmed in the same manner as in Example 7. In the benzoylphenylalanyl[1-$^{13}$C]-leucine methyl ester/γ-cyclodextrin inclusion complex, no diffraction peak inherent to benzoylphenylalanyl[1-$^{13}$C]-leucine methyl ester or γ-cyclodextrin was observed but a halo curve was observed (FIG. 8).

Example 10

Benzoylphenylalanyl[1-$^{13}$C]-leucine methyl ester/γ-cyclodextrin Inclusion Complex Breath Test As in Example 2, a benzoylphenylalanyl[1-$^{13}$C]-leucine methyl ester/γ-cyclodextrin inclusion complex breath test was carried out wherein benzoylphenylalanyl[1-$^{13}$C]-leucine methyl ester/γ-cyclodextrin inclusion complex obtained in Example 9 was orally administered (suspended in 0.5% CMC-Na solution, 70 mg/kg of benzoylphenylalanyl-[1-$^{13}$C]-leucine methyl ester, 5 ml/kg) to chronic pancreatitis and control rats and the time course of the $^{13}$C concentration in the exhaled $CO_2$ after the administration was measured.

Figure 9:
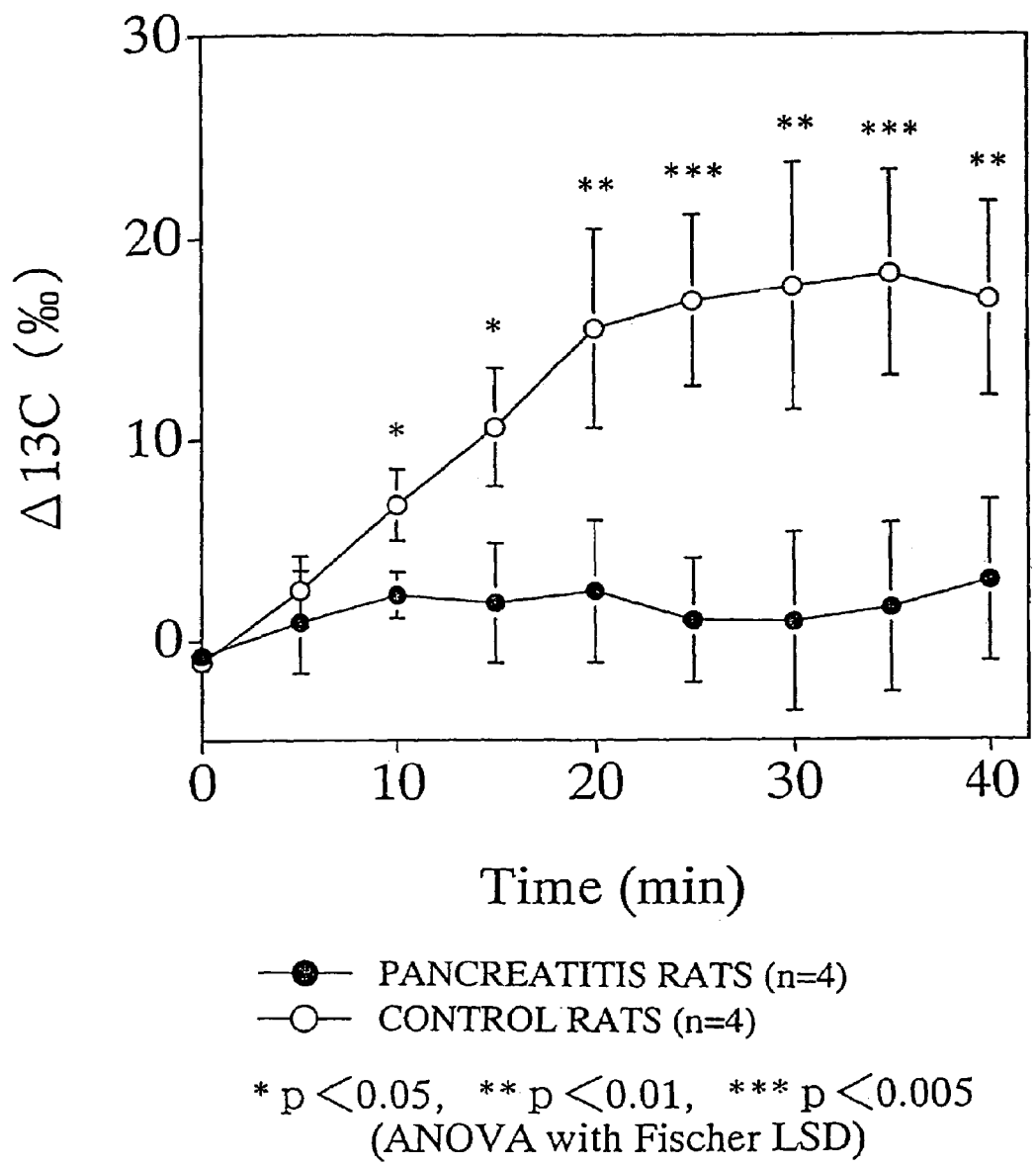
FIG. 9 shows the time course of degree of increase of the $^{13}$C concentration in the exhaled $CO_2$ ($\Delta^{13}C$ (‰)) after administration of benzoylphenylalanyl[1-$^{13}$C]-leucine methyl ester/γ-cyclodextrin (Bz-Phe-($^{13}$C-Leu)Me/γ-CD) inclusion complex. At 0 minute, Bz-Phe-($^{13}$C-Leu)Me/γ-CD was orally administered (70 mg/kg of Bz-Phe-($^{13}$C-Leu)Me) to chronic pancreatitis rats (n=4, M) and control rats (n=4, F). The bar indicates SD.

The $\Delta^{13}$C (‰) values of the chronic pancreatitis rats were smaller than the control rats during 40 minutes (FIG. 9). At 10 minutes after the administration, the $\Delta^{13}$C (‰) value of 2.24±1.32 in the chronic pancreatitis rats was significantly smaller than the value of 6.73±2.06 in the control rats ($p<0.05$, ANOVA with Fischer LSD).

Example 11

Preparation of $^{13}$C-dilaurylfluorescein ($^{13}$C-FDL)

Five grams (5 g) of 1-$^{13}$C-lauric acid (Masstrace) was dissolved in dry chloroform and 20 fold molar amount of thionyl chloride was added thereto. This solution was refluxed under heating for 2 hours and chloroform was removed out by an evaporator. Further, thionyl chloride was-distilled out under reduced pressure and the residue was immediately used in the subsequent reaction. Fluorescein 2Na in a 1/6 molar amount of the lauryl chloride was dissolved in 20 ml of dry acetone and an equal molar amount of pyridine was added and heated at 45° C. The acid chloride obtained above was dropwise added through a dropping funnel over 30 minutes, during which light was shut out and the temperature was kept at 45° C. After the dropping, the mixture was reacted for 2 hours.

After the reaction, acetone was distilled out and chloroform was then added to dissolve the residue. Materials insoluble in chloroform were removed out by filtration and the chloroform phase was washed sequentially with water, alkali, water, acid, and water and dried over sodium sulfate. Chloroform was distilled out and the residue was purified by silica gel column (3 cm×60 cm, chloroform/ether) and active carbon. The resulting compound was washed with cold methanol to yield $^{13}$C-FDL.

The structure and $^{13}$C-labeled position were confirmed by $^{13}$C-NMR and mass spectrometry. $^{13}$C-NMR (heavy chloroform, 300 MHz): 172.2 ppm ($^{13}$COOR) Mass spectrometry (Er-ME) m/z: 698 (M$^+$), 288, 287, 271 LC-MS (APCI) m/z: 699 (M$^+$+H), 516, 333

Example 12

$^{13}$C-FDL Breath Test 12-1 Method

A $^{13}$C-FDL breath test was carried out wherein $^{13}$C-FDL was orally administered to chronic pancreatitis and control rats and the time course of the $^{13}$C concentration in the exhaled $CO_2$ after the administration was measured.

According to Mundlos et al. (Mundlos et al., Pancreas, 1:29 (1986)), the chronic pancreatitis rats were prepared by injecting oleic acid into the pancreatic duct of Wistar male rats of 5 weeks old and kept for 3 weeks. Rats in which midline incision was made on the abdomen were used as the control.

The chronic pancreatitis and control rats of 8 weeks old, which fasted overnight, were fixed without anesthesia in a rat holder for a microwave irradiation apparatus. The breath was collected at a rate of about 100 to 300 ml/min using a $CO_2$ meter (CAPSTER-100) to monitor the $CO_2$ concentration. After the $CO_2$ concentration was stabilized, the rat was once removed out of the rat holder and the $^{13}$C-FDL dissolved in olive oil was administered (160 mg/kg, 4 ml/kg) into the stomach using an oral sonde.

The breath was taken out as a sample immediately before the administration and at every hour for 5 hours after the administration and the $^{13}$C concentration in the exhaled $CO_2$ was analyzed by a gas chromatography-mass spectrometer (GC-MS). The analytic conditions for GC-MS are as follows. The $CO_2$ concentration in the collected breath was held at 3±0.5%. GC-MS conditions:

Apparatus: Shimadzu GC-MS QP-5000 (Shimadzu Corporation)

Column: 0.32 mm×25 m (ID×L) fused silica capillary column PORAPLOT Q (CHROMPACK)

Ionization: EI (electron impact)

Vaporization chamber temperature: 60° C.

Column temperature: 60° C.

GC interphase temperature: 230° C.

Carrier gas: He

Carrier gas pressure: 20 KPa

Measurement mode: SIM (selected ion monitoring)

Measured ion: m/z=45, 46, 47

Amount of sample injected: 25 Φ1

Method for calculation of $^{13}$C concentration

Assuming that the isotopic abundance of oxygen is the same as that which is naturally occurring, $^{13}$C concentration was calculated from the peak areas of the ions m/z=45 and 46 according to the following equation:

$^{13}$C concentration (%)=[0.004176−0.0007462a)/(0.9944396+00034298a)]×100 wherein a is an area ratio (A45/A46) of m/z being 45 and 46 (see Japanese Patent Application Laying Open No. 7-120434).

$\Delta^{13}C$ (‰) was calculated from the $^{13}$C concentration in the exhaled $CO_2$ at each time point ($^{13}$C tmin) and the $^{13}$C concentration in standard $CO_2$ ($^{13}$C std) according to the following equation:

$$\Delta^{13}C\ (‰)=[(^{13}C\ tmin - ^{13}C\ 0\ min)/^{13}C\ std]\times 1000$$

12.2 Results

Figure 10:
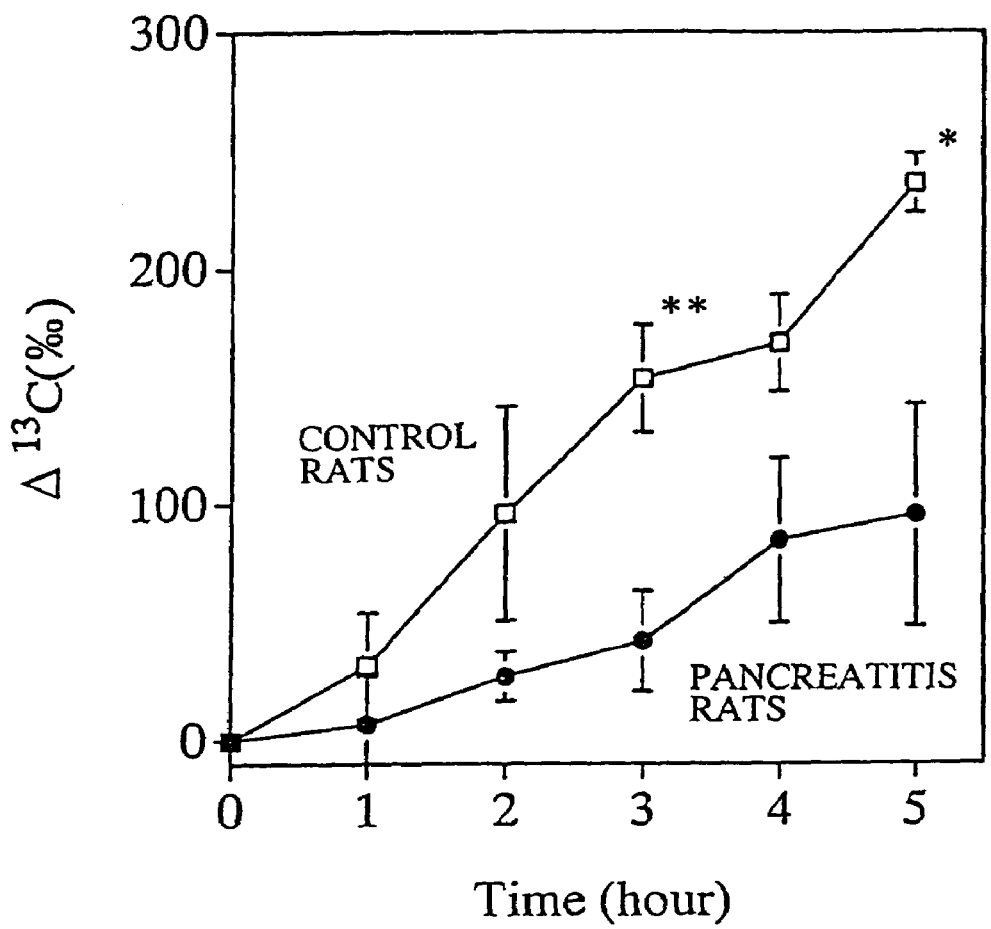
FIG. 10 shows the time course of degree of increase of the $^{13}$C concentration in the exhaled $CO_2$ ($\Delta^{13}C$ (‰)) after administration of $^{13}$C-dilaurylfluorescein ($^{13}$C-FDL). At 0 minute, $^{13}$C-FDL was orally administered (160 mg/kg) to chronic pancreatitis rats (M, n=3) and control rats (~, n=3). Bars represent SD.

In both the control and chronic pancreatitis rats, the $\Delta^{13}C$ (‰) value continued to increase for 5 hours. However, the $\Delta^{13}C$ (‰) values of the chronic pancreatitis rats were smaller than the control rats at each time point for 5 hours (FIG. 10). At 3 hours after the administration, the $\Delta^{13}C$ (‰) value of 42.0±21.3 in the chronic pancreatitis rats was very significantly smaller than the value of 153.3±22.8 in the control rats ($p<0.01$). At 5 hours after the administration, the $\Delta^{13}C$ (‰) value of 95.4±47.1 in the chronic pancreatitis rats was significantly smaller than the value of 236.3±12.4 in the control rats ($p<0.05$).

Example 13

Preparation of $^{13}$C-dioctanoylfluorescein ($^{13}$C-FDO)

Two grams (2 g) of 1-$^{13}$C-octanoic acid (Masstrace) and 1.52 g of fluorescein 2Na were dissolved in dimethylformamuide (DMF) and 9.13 g of benzotriazol-1-yl-oxy-tris(dimethylamino) phosphonium hexafluorophosphate (BOP) and 7.2 ml of diisopropylethylamine (DIEA) were sequentially added and stirred at room temperature for 12 hours. After the completion of the reaction was confirmed by TLC, the reaction mixture was extracted with ethyl acetate. The organic layer was dried, concentrated, purified through a colurn (solvent: 20% ethyl acetate/hexane) under dark, and concentrated to yield 1.05 g of $^{13}$C-FDO.

The structure and $^{13}$C-labeled position were confirmed by $^{13}$C-NMR and mass spectrometry. $^{13}$C-NMR (heavy chloroform, 400 MHz): 171.9 ppm ($^{13}$COOR) Mass spectrometry (El-MS) m/z: 586 (M$^+$), 542, 415, 332, 288, 287, 271

Example 14

$^{13}$C-FDO Breath Test

As in 12-1, a $^{13}$C-FDO breath test was carried out wherein $^{13}$C-FDO dissolved in olive oil was orally administered (200 mg/kg) to chronic pancreatitis and control rats and the time course of the $^{13}$C concentration in the exhaled $CO_2$ after the administration was measured.

Figure 11:
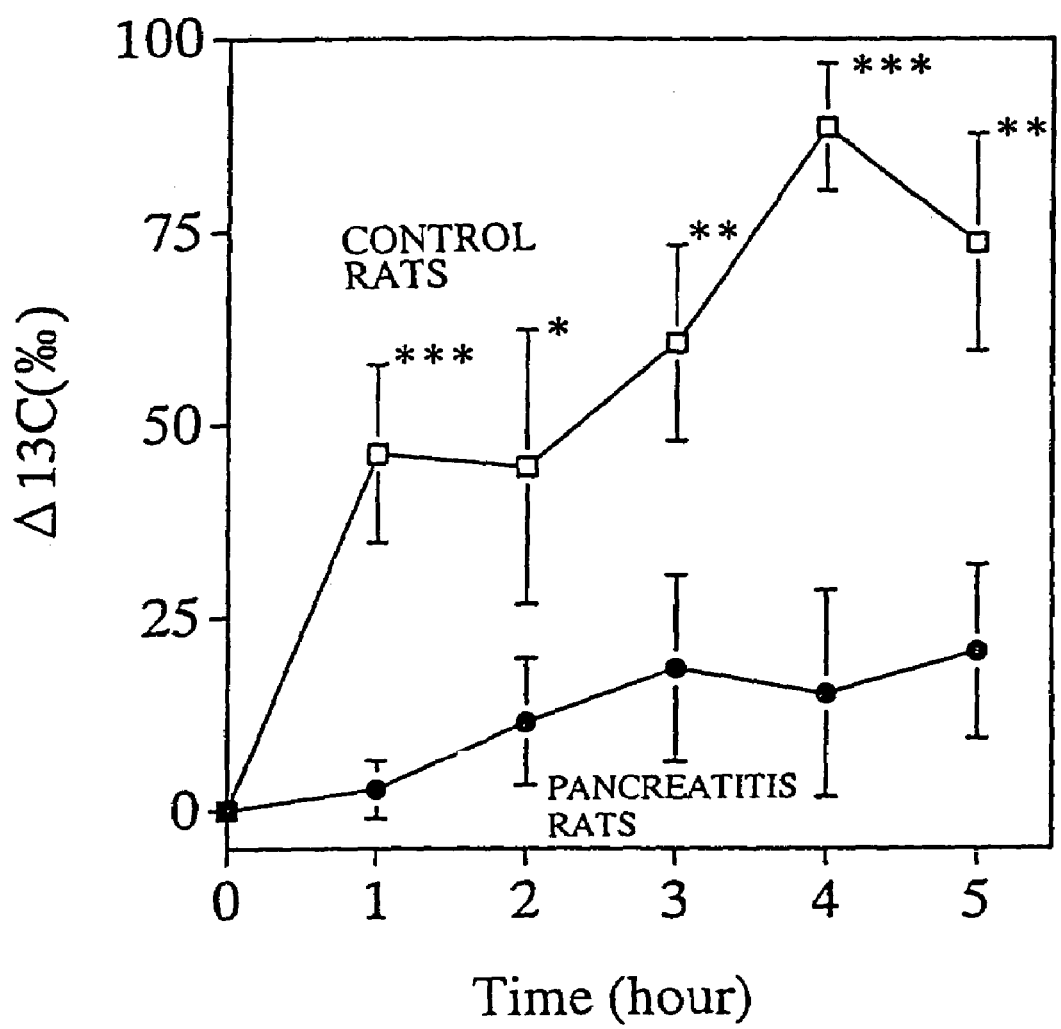
FIG. 11 shows the time course of degree of increase of the $^{13}$C concentration in the exhaled $CO_2$ ($\Delta^{13}C$ (‰)) after administration of $^{13}$C-dioctanoylfluorescein ($^{13}$C-FDO). At 0 minute, $^{13}$C-FDO was orally administered (200 mg/kg) to chronic pancreatitis rats (M, n=4) and control rats (~, n4). Bars represent SD.

The $\Delta^{13}C$ (‰) values of the chronic pancreatitis rats were smaller than the control rats at each time point for 5 hours (FIG. 11). At 1 hour after the administration, the $\Delta^{13}C$ (‰) value of 2.7±3.8 in the chronic pancreatitis rats was very significantly smaller than the value of 46.3±11.5 in the control rats ($p<0.001$). At 3 hours after the administration, the $\Delta^{13}C$ (‰) value of 18.4±12.1 in the chronic pancreatitis rats was very significantly smaller than the value of 60.6±12.7 in the control rats ($p<0.01$). At 4 hours after the administration, the $\Delta^{13}C$ (‰) value of 15.2±13.4 in the chronic pancreatitis rats was very significantly smaller than the value of 88.7±8.2 in the control rats ($p<0.001$). At 5 hours after the administration, the $\Delta^{13}C$ (‰) value of 20.6±11.2 in the chronic pancreatitis rats was very significantly smaller than the value of 73.6±14.1 in the control rats (p<0.01).

Example 15

Preparation of $^{13}$C-diacetylfluorescein ($^{13}$C-FDA)

Two grams (2 g) of 1-$^{13}$C-acetic acid CMasstrace) and 3.63 g of fluorescein 2Na were dissolved in DMF and 15.94 g of BOP and 17.1 ml of DIEA were sequentially added and stirred at room temperature for 12 hours. After the completion of the reaction was confirmed by TLC, the reaction mixture was extracted with ethyl acetate. The organic layer was dried, concentrated, purified through a column (solvent: 20% ethyl acetate/hexane) under dark, and concentrated to yield 1.01 g of $^{13}$C-FDA.

The structure and $^{13}$C-labeled position were confirmed by $^{13}$C-NMR and mass spectrometry. $^{13}$C-NMR (heavy chloroform, 400 MHz): 168.8 ppm ($^{13}$COOR) Mass spectrometry (EI-MS) m/z: 418 (M$^+$), 374, 331, 314, 288, 287, 271

Formulation Example 1

Liquid for Internal Use

Purified water was added to 1.5 parts by weight of $^{13}$C-labeled cyclodextrin to produce a total of 100 parts by weight and this total was dissolved and sterilized through a Millipore filter. The filtrate was placed into a vial bottle and sealed to yield a liquid for internal use.

Formulation Example 2

Liquid for Internal Use $^{13}$C-labeled cyclodextrin was mixed with an equal amount of non-labeled cyclodextrin. Purified water was added to 3 parts by weight of the mixture to produce a total of 100 parts by weight and this total was dissolved and sterilized through a Millipore filter. The filtrate was placed into a vial bottle and sealed to yield a liquid for internal use.

Formulation Example 3

Liquid for Internal Use

Olive oil was added to 4 parts by weight of $^{13}$C-FDL to produce a total of 100 parts by weight and this total was dissolved, placed into a vial bottle and sealed to yield a liquid for internal use.

Advantages of the Invention

The present invention provides a test for pancreatic exocrine function which imparts a low stress on subjects and gives the results in a short period of time.

In the test, a $^{13}$C- or $^{14}$C-labeled oligosaccharide or polysaccharide or a salt thereof or a derivative thereof, or a cyclodextrin inclusion complex or a salt, thereof, $^{13}$C- or 1$^{14}$C-labeled fluorescein ester compound or a salt thereof is used. Among these materials, cyclodextrins and non-reducing terminal modified oligosaccharides or polysaccharides are useful as substrates for evaluating α-amylase secretion ability since they are specific to α-amylase in the digestive tract and are not degraded by α-glucosidase (maltase). These properties are different from those of starch. Further, inclusion complexes using cyclodextrin which is a substrate specific for α-amylase in the digestive tract provide substrates for more universally carrying out a test specific to the disease conditions by selecting the molecules included therein. These methods impart much lower stress on subjects and require less skills for operators compared to the conventional intubation test.

This test method may be utilized in diagnosis for pancreatitis in a collective physical examination, assessment of the seriousness of chronic pancreatitis, precognition of onset of serious fulminant pancreatitis with a still high mortality (30%), diagnosis of causes for pancreatitis, and early diagnosis of pancreatic cancer. Further, it may be useful as a diagnostic method for ruling out pancreatitis in medical examination of general outpatients.

All publications, patents and patent applications cited herein are incorporated herein by reference in their entity.

What is claimed is:

1. A method of diagnosing pancreatic exocrine function comprising:
    administering to a subject a $^{13}$C- or $^{14}$C-labeled inclusion complex or a salt thereof having a cyclodextrin or a modified derivative thereof and having a guest molecule included in a cavity of the cyclodextrin or modified derivative thereof, and
    measuring from the subject a concentration of $^{13}$C- or $^{14}$C-labeled products degraded from the $^{13}$C- or $^{14}$C-labeled inclusion complex ingested by pancreatic exocrin enzymes in the subject,
    wherein the degraded $^{13}$C- or $^{14}$C-labeled products are $^{13}$CO$_2$ or $^{14}$CO$_2$.

2. A method according to claim 1, wherein the $^{13}$C- or $^{14}$C-labeled inclusion complex of salt thereof has any one of the carbons in the guest molecule labeled as $^{13}$C- or $^{14}$C.

3. A method according to claim 1, wherein the guest molecule is selected from the group consisting of: phenol, hydroxy benzoic acid, benzaldehyde, methyl sulfoxide, benzoic acid, aniline, amino benzoic acid, methyl benzoic acid, nitrophenol, pyridine, acetic acid, alcohols, prostandin, benexate hydrocholoride, nitroglycerin, or limaprost.

4. A method according to claim 1, wherein the guest molecule is selected from the group consisting of: an amino acid, fatty acid, organic acid, catechin, vitamin, carotenoid, flavonoid, and cholesterol.

5. A method according to claim 1, wherein the guest molecule is selected from the group consisting of an oligosaccharide, peptide, and fatty acid glyceride.

6. A method according to claim 1, wherein the $^{13}$C- or $^{14}$C-labeled inclusion complex is selected from the group consisting of phenylalanine/β-cyclodextrin, tryptophan/α-cyclodextrin, histidine/α-cyclodextrin, cinnalidine/β-cyclodextrin, ferulic acid/β-cyclodextrin, and phenylalanyl leucine/β-cyclodextrin.

7. A method according to claim 1, wherein the $^{13}$C- or $^{14}$C-labeled inclusion complex or a salt thereof is administered to the subject such that the ratio of the cyclodextrin or modified derivative thereof to the guest molecule is one to one.

8. A method of diagnosing pancreatic exocrine function comprising:
    administering a $^{13}$C- or $^{14}$C-labeled inclusion complex or a salt thereof having a cyclodextrin or a modified derivative thereof and having a guest molecule included in the cyclodextrin or modified derivative thereof, wherein any one of the carbons in the guest molecule is labeled as $^{13}$C- or $^{14}$C and
    measuring from the subject a concentration of $^{13}$C- or $^{14}$C-labeled products degraded from the $^{13}$C- or $^{14}$C- labeled inclusion complex ingested by pancreatic exocrine enzymes in the subject,
wherein the degraded $^{13}$C- or $^{14}$C-labeled products are $^{13}$CO$_2$ or $^{14}$CO$_2$.

9. A method according to claim 8, wherein the guest molecule is selected from the group consisting of: phenol, hydroxy benzoic acid, benzaldehyde, methyl sulfoxide, benzoic acid, aniline, amino benzoic acid, methyl benzoic acid, nitrophenol, pyridine, acetic, acid, alcohols, prostandin, benexate hydrocholoride, nitroglycerin, or limaprost.

10. A method according to claim 8, wherein the guest molecule is selected from the group consisting of: an amino acid, fatty acid, organic acid, catechin, vitamin, carotenoid, flavonoid, or cholesterol.

11. A method according to claim 8, wherein the guest molecule is selected from the group consisting of an oligosaccharide, peptide, and fatty acid glyceride.

12. A method according to claim 8, wherein the $^{13}$C- or $^{14}$C-labeled inclusion complex is selected from the group consisting of phenylalanine/β-cyclodextrin, tryptophan/α-cyclodextrin, histidine/α-cyclodextrin, cinnalidine/β-cyclodextrin, ferulic acid/β-cyclodextrin, and phenylalanyl leucine/ β-cyclodextrin.

13. A method according to claim 8, wherein the $^{13}$C- or $^{14}$C-labeled inclusion complex or a salt thereof is administered to the subject such that the ratio of the cyclodextrin or modified derivative thereof to the guest molecule is one to one.

14. A method of diagnosing pancreatic exocrine function comprising:
administering to a subject a $^{13}$C- or $^{14}$C-labeled inclusion complex or a salt thereof having a cyclodextrin or a modified derivative thereof and having a guest molecule included in the cyclodextrin or a modified derivative thereof, wherein any one of the carbons in the guest molecule is labeled as $^{13}$C- or $^{14}$C, and the $^{13}$C- or $^{14}$C-labeled inclusion complex or a salt thereof is administered to a subject such that the ratio of the cyclodextrin or a modified derivative thereof to the guest molecule is one to one and
measuring from the subject a concentration of $^{13}$C- or $^{14}$C-labeled products degraded from the $^{13}$C- or $^{14}$C-labeled inclusion complex ingested by pancreatic exocrine enzymes in the subject,
wherein the degraded $^{13}$C- or $^{14}$C-labeled products are $^{13}$CO$_2$ or $^{14}$CO$_2$.

15. A method according to claim 14, wherein the guest molecule is selected from the group consisting of: phenol, hydroxy benzoic acid, benzaldehyde, methyl sulfoxide, benzoic acid, aniline, amino benzoic acid, methyl benzoic acid, nitrophenol, pyridine, acetic, acid, alcohols, prostandin, benexate hydrocholoride, nitroglycerin, or limaprost.

16. A method according to claim 14, wherein the guest molecule is selected from the group consisting of an amino acid, fatty acid, organic acid, catechin, vitamin, carotenoid, flavonoid, and cholesterol.

17. A method according to claim 14, wherein the guest molecule is selected from the group consisting of an oligosaccharide, peptide, and fatty acid glyceride.

18. A method according to claim 14, wherein the $^{13}$C- or $^{14}$C-labeled inclusion complex is selected from the group consisting of phenylalanine/β-cyclodextrin, tryptophan/α-cyclodextrin, histidine/α-cyclodextrin, cinnalidine/β-cyclodextrin, ferulic acid/β-cyclodextrin, and phenylalanyl leucine/β-cyclodextrin.

* * * * *